United States Patent
Lopez Canovas et al.

(10) Patent No.: US 7,731,828 B2
(45) Date of Patent: Jun. 8, 2010

(54) METHOD FOR RAPID TYPIFICATION OF MICROORGANISMS AND SET OF REAGENTS USED

(75) Inventors: Lilia Lopez Canovas, Habana (CU); Ana Maria Riveron Rojas, Habana (CU); David Higgison Clarke, Habana (CU); Axel Sánchez Alonso, Habana (CU); Esther Orozco Orozco, Mexico City (MX); Oscar Arencibia Diaz, Habana (CU); María Concepción Ariosa Acuña, Habana (CU); Hilda Teresa Clark Dondériz, Habana (CU); Regnar Gigato Pérez, Habana (CU)

(73) Assignee: Centro Nacional de Investigaciones Cientificas (CNIC) (CU)

( * ) Notice: Subject to any disclaimer, the term of this patent is extended or adjusted under 35 U.S.C. 154(b) by 1035 days.

(21) Appl. No.: 10/415,950

(22) PCT Filed: Nov. 2, 2001

(86) PCT No.: PCT/CU01/00008
§ 371 (c)(1),
(2), (4) Date: Oct. 20, 2003

(87) PCT Pub. No.: WO02/38802
PCT Pub. Date: May 16, 2002

(65) Prior Publication Data
US 2004/0050700 A1 Mar. 18, 2004

(30) Foreign Application Priority Data
Nov. 7, 2000 (CU) .............................. 2000/0247

(51) Int. Cl.
*G01N 27/447* (2006.01)
*C12Q 1/68* (2006.01)
*C12N 1/06* (2006.01)

(52) U.S. Cl. ................ 204/458; 204/468; 204/609

(58) Field of Classification Search ............ 204/458, 204/468, 609
See application file for complete search history.

(56) References Cited

U.S. PATENT DOCUMENTS

| 4,473,452 A | 9/1984 | Cantor et al. |
| 4,707,237 A * | 11/1987 | Lepp et al. ............... 204/466 |
| 4,861,448 A | 8/1989 | Cantor et al. |
| 5,795,455 A | 8/1998 | Pannetier |
| 6,203,679 B1 * | 3/2001 | Bouis et al. ............... 204/466 |

FOREIGN PATENT DOCUMENTS

| GB | 2249395 A | 5/1992 |
| WO | WO 95/14768 A | 6/1995 |

OTHER PUBLICATIONS

Riveron, A.M., et al. Analytical Letters, vol. 28, No. 11, pp. 1973-1991, 1995.
Riveron, A.M., et al. Analytical Letters, vol. 28, No. 5, pp. 845-860, 1995.
Lopez-Canovas, L. et al. Analytical Letters, vol. 29, No. 12, pp. 2079-2084, 1996.

(Continued)

*Primary Examiner*—Kaj K Olsen
(74) *Attorney, Agent, or Firm*—Lackenbach Siegel, LLP

(57) ABSTRACT

A process for rapid typing of yeast, parasites and bacteria is provided. It comprises the following steps: a) Preparing immobilized intact DNA in 5 to 60 minutes aided by a method involving a reagent kit that only contains buffer solution, a detergent, a metal chelating agent and an agent to disrupt the hydrogen bonds. b) Separating intact DNA molecules or their restriction fragments in miniequipments for Pulsed Field Gel Electrophoresis of the CHEF (Contour Clamped Homogeneous Electric Field) and TAFE (Transversal Alternating Field Electrophoresis) systems in times comprised between 2.5 and 7 hours. c) Selecting the optimal conditions that should be set in miniCHEF with the aid of a method to simulate the electrophoresis patterns d) Providing reorientation times, migration velocities and sizes of the molecules calculated with the aid of a method to analyze the migrated distances without the use of size markers.

32 Claims, 10 Drawing Sheets

Scheme of the Mold to Cast the Miniplugs

OTHER PUBLICATIONS

Lopez-Canovas, L. et al. Journal of Chromatography A, vol. 806, No. 1, pp. 123-139, May 8, 1998.

Higginson D., et al. Analytical Letters, vol. 27, No. 7, pp. 1255-1264, 1994.

Riveron, A.M., et al. European Biophysics Journal, vol. 29, No. 1, pp. 48-56, 2000.

Schwartz, D.C., et al. Cell, vol. 37, No. 1, pp. 67-75, 1984.

Journal of Clinical Microbiology, Mar. 1999, p. 876-877, vol. 37, No. 3; Critical Observations on . . . ; Gianluigi Cardinali, Carlo Tascini et al.

Journal of Clinical Microbiology, Jun. 1998, p. 1653-1659, vol. 36, No. 6; Assessment of Resolution and Intercenter . . . Alex Van Belkum, et al.

Journal of Clinical Microbiology, Feb. 1999, p. 380-385, vol. 37, No. 2, Pulsed-Field Gel Electrophoresis is More . . . Angeli Kodjo et al.

Journal of Clinical Microbiology, Jan. 2000, p. 351-353; Simplified Protocol for Pulsed-Field Gel . . . M. Catherine McEllistrem, Janet E Stout, et al.

Journal of Clinical Microbiology,, Jan. 2000, p. 464-465, Fast-Track Communication Achieving 100% Typeability of Pseudomonas . . . Ute Romlin, et al.

Molecular and Cellular Biology, Jun. 1991, p. 3348-3354; Pulsed-Field Electrophoresis of Mega . . . Kevin Gunderson et al.

Journal of Clinical Microbiology, Sep. 1995, p. 2233-2239, Interpreting Chromosonal DNA Restriction Patterns Produced by . . . Fred C. Tenover et al.

Dept. of Pathology, University of Iowa College of Medicine Iowa City, In Vitro Susceptibility Testing and DNA typing of Saccharomyces . . . L Zerva, RJ Hollis et al.

A Companion to Methods in Enzymology, vol. 1, No. 2 Oct. 1990, pp. 195-203; Genomic Long-Range Restriction Mapping; Douglas R Smith.

Journal of Chromatography A. 806 (1998) 187-197; Comparison of DNA Migrations in Two Clamped Homogeneous Electric Field . . . L. Lopez-Canovas, R. Biscay et al.

Molecular Biotechnology, vol. 9, 1998, p. 107-126; Pulsed-Field Gel Electrophoresis; John Maule.

Switch Intervals and Resolutionin Pulsed Field Gels (Chapter 6).

Variables that Affect Pulsed Field Gels (Chapter (8).

Bio-Rad Chef Mapper XA Pulsed Field Electrophoresis System; Instruction Manual; Catalog Nos. 170-3670-3673.

La Recherche Mensuel No. 314 Nov. 1998 38 France; La fin de l'age d'or des antibiotiques; Jacques Acar Et Patrice Courvalin.

La Recherche Mensuel No. 314 Nov. 1998 38 France; La Surveillance S'organise; Helene Aubry-Damon Et Antoine Andremont.

La Recherche Mensuel No. 314 Nov. 1998 38 France;; Visite Guide au Coeur de L'arsenal Bacterien; Patrick Trieu-Cuot Et Claire Poyart.

Bio-Rad Laboratores; Life Science Research Products 1998/99; Nucleic Acid Electrophoresis, p. 185.

* cited by examiner

Scheme of the Mold to Cast the Miniplugs

Photograph of S. cerevisiae and H. polymorpha chromosomal band patterns separated in the MiniCHEF and miniTAFE minigels.

Band patterns obtained in the miniCHEF for the Xba 1 macrorestriction DNA fragments of P. aeruginosa.

Band patterns given by MiniCHEF for Sma 1 macrorestriction DNA fragments of S. aureus.

Photograph of the DNA band patterns of E. hostolytica, S. cerevisiae and 015 phage concatamers.

Photograph of real miniCHEF minigel (40) used to obtain the ban patterns of s. cerevisiae 196-2 chromosomes (left) and graphic of the hypothetical minigel (42 predicted by the simulator (right).

Flow chart of the method to simulate the DNA band patterns in the minigels of the miniCHEF.

Electrophoresis karyotype (61 obtained in the miniCHEF for S. cerevisiae chromosomes.

Flow chart of the method that needs to be fed with migrated distances to estimate the size (kb), reorientation times (tr).

MiniCHEF typing of the INN3 and INN7 E. coli isolates after Xba I restriction digestion of their DNA molecules.

METHOD FOR RAPID TYPIFICATION OF MICROORGANISMS AND SET OF REAGENTS USED

This application is the national phase under 35 U.S.C. §371 of PCT International Application No. PCT/CU01/00008 which has an International filing date of Nov. 2, 2001, which designated the United States of America.

DESCRIPTIVE MEMORY

INTERNATIONAL PATENT CLASSIFICATION INDEX: C12N 1/00

REFERENCE TO RELATED APPLICATION

This application is a 371 National Stage Entry of PCT/CU01/00008 filed on Nov. 2, 2001.

The present invention is related to molecular biology. In particular, a process is provided. Said process includes the use of methods and procedures, as well as a reagent kit for rapid microorganism typing. The microorganisms to be typed can be yeast, parasites and bacteria Gram-positive or Gram-negative. The microorganism typing is done by Pulsed Field mini-Gel Electrophoresis performed in miniequipments of CHEF or TAFE system.

BACKGROUND OF THE INVENTION

During the past years, infectious diseases have increased and multi-drug resistance microorganisms have arisen (Acar J and Courvalein P pp 50-53; Aubry-Damon H and Andremot A, pp 54-55; Trieu-Cout P and Poyart C, pp 62-66, in 'La Recherche', vol 314, 1998).

Outbreaks of infectious diseases have generated the necessity of typing the causative microorganisms. Typing is the process by which different species of microorganisms of a given genus are classified in different subgroups or subtypes (Busch U and Nitschko H, J Chromatogr B, 1999, 722:263-278). Typing is important, from the epidemiological point of view, for recognizing outbreaks of infection, determining the way of transmission of nosocomial pathogens in the health centers and detecting the sources of the infections. It is also useful for identifying new virulent strains and monitoring vaccination programs. A typing process is been considered adequate if it fulfill the following criteria (Maslow J N et al., Clin Infect Dis, 1993, 17:153-164):

1. To give unambiguous results for each isolate analyzed.
2. To give reproducible results.
3. To differentiate unrelated strains within specie.

There are several microorganism typing methods. Some of them are based on the analysis of phenotypic features (phenotypic methods) and others on the analysis of genotypic features (genotypic methods). Phenotypic methods detect features expressed by microorganisms, whereas the genotypic ones evidence the differences among the DNA of microorganisms. Thus, phenotypic methods have the disadvantage of giving an indirect measure of the changes in the genetic background. Said disadvantage does not occur with the use of genotypic methods.

One of the genotypic typing methods most widely used is Pulsed Field Gel Electrophoresis (PFGE). This method is considered the gold standard for the molecular typing of microorganisms. PFGE typing is performed by separating in gels DNA molecules that are subjected to the action of electric pulses in two different directions. After electrophoresis, the band patterns given by DNA molecules of an isolate of microorganism are highly reproducible and discriminatory and characterize unequivocally its DNA (Oliver D M and Bean P, J Clin Microbiol, 1999, 37(6):1661-1669). Additionally, the whole genomes of numerous isolates can be compared in a single gel. Thus, PFGE has been proposed as the optimal typing method (Maslow J N, Mulligan M E and Arbeit R D, Clin Infect Dis, 1993(17):153-164; Busch U and Nitschko H, J Chromatogr B, 1999(722):263-278). The results obtained by PFGE depend on the experimental conditions applied in DNA separation and on the genus and specie of the microorganism subjected to study. Thus, a) If the microorganism has several lineal chromosomes of sizes lower than 10 Mb (1 megabase=1 000 000 base pairs) the band pattern given by its chromosomes is obtained. Said band pattern is called 'the electrophoretic karyotype'. For instances, the microorganism can be yeast, unicellular parasites, etc.

b) If the microorganism has a single large circular chromosome the band pattern given by the macrorestriction fragments of said circular DNA is obtained. These patterns are called pulsetypes, since they are obtained in specific experimental conditions. For instances, the microorganism can be bacteria such as *Escherichia coli, Staphylococcus aureus*, etc.

The comparison of the electrophoretic karyotypes of different strains permits their characterization and differentiation. The same occurs with the restriction fragments of the bacterial DNA. Thus, both, the molecular karyotypes and the pulsotypes are used in the comparative study of fungi, bacteria and parasites. The routinely use of PFGE in medical microbiology has generated the necessity of improving the methods of sample preparation.

It also generated the need of designing a priori the running conditions to adequately separate the molecules and for analyzing the resulting electrophoresis patterns.

In general, the process of microorganism typing by PFGE comprises the following steps and procedures:

1) Preparing the samples: growing the microorganisms in nutrient broth, embedding the cells in gel and obtaining immobilized and deproteinized intact DNA molecules.
2) Designing the electrophoresis run: selecting the experimental conditions that should be set in PFGE equipments to obtain the optimal separation between the molecules.
3) Loading the samples in the gels and performing pulsed field gel electrophoresis to separate the DNA molecules.
4) Analyzing the band patterns obtained after the electrophoresis and comparing the results given by different isolates of microorganisms.

The equipments and procedures currently used in microorganism typing by PFGE are analyzed.

Pulsed Field Gel Electrophoresis

Pulsed field gel electrophoresis (PFGE) dates from 1984, when Schwartz and Cantor (Cell, 37, 67-75, 1984; U.S. Pat. No. 4,473,452) observed that applying electric pulses that periodically switched their orientation by a certain angle in relation to the agarose gel, large intact DNA molecules were resolved as band patterns.

The authors also determined that the separations of the molecules essentially depend on the duration of the electric pulses. Later, the angle formed by the field force lines, the electric field strength, the experimental temperature, the ionic strength of the buffer solution, the concentration of the agarose gel and the thickness of the agarose plugs, where the samples are embedded, were determined as the most important factors that influenced the resolution of DNA molecules. (Birren B. and Lai E. Pulsed Field Gel Electrophoresis: a practical guide. Academic Press. New York, 1993, p 107, 111, 129, 131, 135; López-Cánovas L. et al., J. of Chromatogr. A, 1998, 806, 123-139; López-Cánovas L. et al., J. of Chromatogr. A, 1998, 806, 187-197).

Different systems to perform PFGE have been developed. They have characteristic chambers with electrodes placed in different arrangements. Among these chambers are the OFAGE (Orthogonal Fi Id Alternating Gel Electrophor sis, Carle C. F. and Olson M. V. Nucleic Acids Res. 1984, 12, 5647-5664) CHEF ('Contour Clamped Homogeneous Electric Field', Chu G. Science 234, 1986, 1582-1585), TAFE ('Transversal Alternating Field Electrophoresis', U.S. Pat. No. 4,740,283), FIGE ('Field Inversion Gel Electrophor sis', U.S. Pat. No. 4,737,251 of Carle G. F. and Olson M. V) arrangements of electrodes, and the minichambers Mini-TAFE and MiniCHEF (Riverón, A. M. et al., Anal. Lett, 1995, 28, 1973-1991; European Patent Application EP 0 745 844, Bula. 1996/49; U.S. patent application Ser. No. 08/688,607, 1995; Cuban patent RPI Nro. 02/95, 1995).

Commonly Used Systems for Microorganism Typing by PFGE

The most used systems for microorganism typing based on DNA analysis by PFGE are CHEF and TAFE. They provide straight band patterns in every lane of the gel, and thus, allow the comparison of the results obtained in a single run or in different electrophoresis runs.

The electrodes of CHEF system are placed in a hexagonal array around the gel and the voltages are clamped in them to guarantee homogenous electric field throughout the gel. The generation of homogeneous electric field throughout the chamber permits to obtain straight bands and reproducible migrations in the lanes of the gel. The electrodes of opposed polarities are 33.5 cm separated in CHEF chambers. It uses submarine gels that can be up to 21×14 cm in width and length. The gels are placed horizontally (CHEF Mapper XA Pulsed Field Electrophoresis System. Instruction Manual and Application Guide. Catalog Numbers 170-3670 to 170-3673, BioRad, pp 11, 1995). As mentioned, CHEF systems have been extensively used for microorganism typing. For instances, bacteria (Beverly, S, Anal Biochem, 1989, 177: 110-114; Dingwall A and Shapiro L, Proc Natl Acad Sci USA, 1989, 86:119-123; Ferdows M S and Barbour A G, Proc Natl Acad Sci USA, 1989, 86:5960-5973; Kohara Y, Akiyma K and Isono K, Cell, 1987, 50:495-508; Ohki M and Smith Cl, Nucleic Acids Res, 1989, 17:3479-3490; Schoenline P V, Gallman L M and Ely B, Gene, 1989, 70:321-329; Ventra L and Weiss A S, Gene, 1989, 78:29-36), Pseudomonas (Bautsch W, Grothues D and Tummler B, FEMS Microbiol Lett, 1988, 52:255-258; Romling U and Tummler B, J Clin Microbiol, 2000, 38(1):464-465), S. cerevisiae (Albig W and Entian K D, Gene, 1988, 73:141-152; Zerva L et al., J Clin Microbiol, 1996, 34(12):3031-3034), E. histolytica (Petter R et al., Infect Immun, 1993, 61(8):3574-3577), S. pneumoniae (McEllistrem M C et al., J Clin Microbiol, 2000, 38(1):351-353), S. aureus (Wichelhaus T A et al., J Clin Microbiol, 1999, 37(3):690-693), M. tuberculosis (Singh S P t al., J Clin Microbiol, 1999, 37(6):1927-1931), P. haemolytica (Kodjo A et al., J Clin Microbiol, 1999, 37(2):380-385), etc.

Due to the large dimensions of the CHEF chamber, it requires large amount of buffer solution to cover its electrode platform. Thus, the current intensity in the chamber can reach high values, even when low electric fields intensities are applied. Therefore, CHEF experiments demand power supplies of high rated power output. Besides it, large amount of heat is generated in the chambers, avoiding the reduction of run duration by increasing the electric field. CHEF chambers need at least 20 hours of electrophoresis to separate *Saccharomyces cerevisiae* chromosomes (molecules smaller than 1.6 Mb. 1 Mb=$10^6$ base pairs) in the characteristic pattern of 11 bands, and to type different strains of this yeast (Zerva L, et al., J Clin Microbiol, 1996, 34(12): 3031-3034). The CHEF chamber takes long time for separating the macrorestriction fragments of bacterial DNA molecules, since 20 hours, or more, are needed (van Belkum A et al., J Clin Microbiol 1998, 36(6):1653-1659; Marchadin H et al., Antimicrob Agents Chemother, 2000, 44(1):213-216; Romling U and Tummler B, J Clin Microbiol, 2000, 38(1):464-465). Similarly, long running times are needed to study parasites such as *Entamoeba histolytica*. To separate its chromosomes 24 hours are needed, at least (Petter R et al., Infect Immun, 1993, 61(8): 3574-3577).

The advantage of currently used CHEF equipments is the possibility of analyzing 40 samples in a single run. This high throughput sample format facilitates the comparative analysis of the electrophoresis patterns given by samples of numerous isolates.

The TAFE system was proposed by K J Gardiner, W Laas and D Patterson in the paper published in Somatic Cell Mol Genet, 1986(12): 185. They called initially the system as "Vertical Pulsed Field Electrophoresis" (VPFE) and developed the equipment that was protected by the U.S. Pat. No. 4,740,283 of Apr. 26, 1988.

In TAFE system, two electrode pairs are placed parallel to both faces of the submarine gel (10×7.6×0.64 cm, length× width×thick), that is placed vertically in the chamber. Said electrode disposition generates electric field force lines that cross transversally the gel and compels the molecules to migrate through the gel thickness during each pulse. In TAFE, homogeneously sized molecules travel similar distances and migrate up to the same height in the gel leaving straight tracks, regardless the positions of the wells (into which the samples were loaded) in the gel. Thus, this system is useful for microorganism typing, since it facilitates the comparative analysis of the electrophoresis patterns given by samples of numerous isolates.

Based on these principles, Beckman Instruments manufactured the equipment called "Geneline I, or Transverse Alternating Field Electrophoresis System" (Beckman, The Geneline System Instruction Manual, ed. Spinco Division of Beckman Instruments Inc., 1988), which is also known as TAFE. This system uses a gel (11×7.2×0.6 cm, length× width×thickness) into which 20 samples can be loaded. Nevertheless, TAFE also requires large amount of buffer solution (3.5 liters) and biological sample. The equipment demands, at least, 20 hours to resolve the *E. histolytica* chromosomes (Báez-Camargo M et al., Mol Gen Genet 1996, 253:289-296). So, TAFE share the drawbacks with CHEF in microorganism typing.

As a conclusion, the commercially available equipments most frequently used to characterize the genome of microorganisms and parasites require long running time, and large amount of reagents and biological samples to resolve large DNA molecules in their band pattern.

FIGE system has been used for rapid typing of bacteria (Goering R V and Winters M A, J Clin Microbiol, 30(3):577-580, 1992; Grothues D et al., J Clin Microbiol, 26(10):1973-19771988). However, electrophoretic mobility inversion of DNA has been documented in FIGE experiments. Mobility inversion of DNA prevents correct size estimations and makes difficult the interpretation and comparison of the patterns given by numerous samples. The impossibility of predicting the moment of occurrence of DNA mobility inversion is one of the problems associated with said phenomenon (Birren B and Lai E. Pulsed Field Gel Electrophoresis: a practical guide, pp 10, Academic Press, Inc. San Diego, Calif. 1993). The main disadvantage of mobility inversion is the impossibility of identifying unambiguously the molecules present in a given band. To do it, the bands should be transferred and hybridized with specific probes. Hybridization notably increases the prices of the assay and is time demanding, thus the typing process will be more expensive and time consuming.

The attempts to reduce the electrophoresis time in current CHEF equipments, such as GeneNavigator (Amersham-Pharmacia-LKB, Pharmacia Molecular and Cell Biology Catalogue, Pulsed Field Gel Electrophoresis, Nucleic Acids Electrophoresis. 1998, pp 77-79), CHEF DRII and CHEF Mapper (CHEF Mapper XA Pulsed Field Electrophoresis System. Instruction Manual and Application Guide. Catalog Numbers 170-3670 to 170-3673. Bio-Rad, pp 11, 1995) by increasing the voltage applied to the electrodes is nearly impossible. It is due to the limit of power supply output and the cooling system. Consequently, manufacturers recommend 9 V/cm as maximum electric field to apply in said equipments (CHEF Mapper XA Pulsed Field Electrophoresis System. Instruction Manual and Application Guide. Catalog Numbers 170-3670 to 170-3673. Bio-Rad, pp 2, 1995). Therefore, the reduction of the electrophoresis duration by increasing the electric field intensity is prevented in CHEF system. Current TAFE equipments have similar problems.

PFGE Miniequipments

MiniPFGE equipments, miniCHEF and miniTAFE versions, were reported in 1995 (Riverón A M et al., Anal. Lett., 1995, vol. 28, pp 1973-1991; European Patent Application EP 0 745 844, Bull. 1996/49; U.S. patent application Ser. No. 08/688,607, 1995; Cuban Patent RPI 02/95, 1995). Miniequipments overcome most of the mentioned drawbacks of the PFGE equipments. Pulsed field electrophoresis experiments are performed in a minigel (4×4×0.5 cm; length× width×thickness) loaded with 7 samples in 4 to 6 hours. Electric field strength reaching 16 V/cm can be applied in MiniCHEF, providing good resolution of the electrophoresis band patterns in 2.7 hours. The short distance between the electrodes of opposed polarities permits to construct small chambers and to use small amount of buffer volumes to cover the electrodes. By applying a given voltage to a miniCHEF and CHEF chambers (certain electric field strength value 'E') the heat generated in the minichamber is always lesser than the heat generated in the commercially available CHEF (Riverón A M et al., Anal. Lett., 1995 vol. 28, pp. 1973-1991).

MiniTAFE equipments admit 22 V/cm, achieving resolution among the bands (Riverón A M et al., Anal. Lett., 1995 vol. 28, pp. 1973-1991). MiniTAFE permits to obtain the *S. cerevisiae* electrophoretic karyotype in 5 hours. MiniTAFE chambers with short separation (7.8 cm) between opposite electrodes are small and use small amount of buffer solution. However, if samples thicker than 0.1 cm are loaded in the minigels, longer running times are needed to achieve good resolution of the electrophoresis patterns. According to previous reports, sample thickness influences electrophoresis running time (López-Cánovas et al., J. Chromatogr. A, 1998, 806, pp. 187-197). As the samples are thicker, longer gels are needed to obtain the same band patterns. However, the reported miniCHEF minigels admit only 7 samples, whereas the miniTAFE supports 13 samples. They are low throughput sample formats for typing isolates of microorganisms in clinical laboratories.

Despite miniPFGE equipments have advantages over currently used systems, neither miniCHEF nor MiniTAFE were used for microorganism typing. Maybe, it obeys to the attempting of using samples as thick as the ones used in conventional gels. In addition, simple procedures to select miniequipment running parameters are not available.

Preparation of Immobilized DNA

A method to prepare intact DNA molecules is essential for microorganism typing by PFGE in current equipments or miniequipments. Previously reported methods of DNA isolation and purification in solution provoke shearing of said molecules (Schwartz D C and Cantor C R, Cell, 1984, 37, pp. 66-75). Schwartz and Cantor proposed a methodology to prepare samples for PFGE and only excluded the molecules with sizes smaller than 1 Mb ($10^6$ base pairs). The methodology consists in harvesting the cultured cells, washing the cells and embedding them in agarose plugs. In ulterior steps, spheroplasts (if cellular wall exists) are formed 'in situ' and further lysed in said plugs. Finally, the immobilized DNA molecules are deproteinized using proteinase K. The method has been effective to prepare samples from microorganisms of different genus, species and origins. However, spheroplasts need to be formed if said microorganisms possess cell wall, and the enzymes needed to form spheroplasts, as well as the proteases, are expensive. The reported procedure requires that samples were incubated overnight twice, which is 32 hours for sample preparation (U.S. Pat. No. 4,473,452, Sep. 25, 1984).

More recently, Gardner (Gardner D C J et al., Yeast, 1993, 9, 1053-1055) obtained band patterns of *S. cerevisiae* chromosomes from cells that did not form spheroplasts. In parallel, Higginson et al (Higginson D. et al., Anal. Lett., 1994, 27:7, 1255-1264) showed that *S. cerevisiae* DNA can be deproteinized using 8 M urea instead of proteinase K. However, the method described by Gardner is still expensive, because he used proteases to deproteinize the DNA, whereas, the method described by Higginson is cheap, but consumes 72 hours of incubation, which is a long time. Later, *S. cerevisiae* samples were prepared, and enzymes were not used: The plugs were sequentially incubated with LETK (10 mM Tris, 500 mM EDTA, 600 mM KCl, pH 7.5) for 4 hours, NDS (10 mM Tris, 500 mM EDTA, 1% sarcosyl, pH 9.5) for 2 hours, and NDS plus 4 M urea (NDSU) for 2 hours. This method needed 10 hours for sample preparation (López-Cánovas L, et al., Anal. Lett, 1996, 29:12, 2079-2084). Rapid methods for the preparation of immobilized DNA were described also, but they use enzymes (for instance, in Guidet F and Langridge P, Biotech, 1992, 12:2, 222-223).

As general rule, immobilized DNA for PFGE experiments requires the formation of spheroplasts and DNA deproteinization using proteases. These requirements are independent from the cell type studied (bacteria, yeast, etc) (Maule J, Mol. Biotech. 1998, 9: 107-126; Olive D M and Bean P, J. Clin. Microbiol, 1996, 37:6, 1661-1669). For instances, immobilized *Staphilococcus aureus* DNA were reported to be prepared in 2 hours by immobilizing cells with lysostaphin and incubating the plugs with detergents, whereas *Streptococcus fecalis* cells needed to be incubated with lysozyme and mutanolysin prior to the immobilization (Goering R V. and Winter M A., J. Clin. Microbiol, 1992, 30:3, 577-580). In the mentioned work, authors did not incubate the samples with proteinase K. However, Matushek et al. (Matushek M G et al., J. Clin. Microbiol, 1996, 34:10, 2598-2600) reported that they were unable to obtain the band patterns if the samples were not incubated with proteinase k. As alternative, they proposed a rapid method to prepare immobilized DNA samples using proteinase K. Recently, McEllistrem et al. (McEllistrem M C et al., J. Clin. Microbiol, 2000, 38:1, 351-353) reported a complete non-enzymatic method to prepare immobilized DNA of *Streptococcus pneumoniae*. However, it consumes 6 hours and the authors attributed the protocol success to the activation of an autolysin of the *Streptococcus*. At present, the spheroplast formation enzymes and the proteases have been deleted only from the protocols of preparation of intact DNA molecules of *S. cerevisiae* and *Streptococcus pneumoniae*, but the times required to complete these preparations are 10 and 6 hours, respectively, which are long times. Consensus does not exist about the feasibility of deleting the protoplast formation enzymes and proteinase K in sample preparation of microorganisms. Therefore, current methods are expensive and consume long times.

Most of the above methods rest on the assumption that microorganisms with cell walls must be immobilized previously to the enzymatic treatment. An exception is presented in the paper published by Goering and Winter (Goering R V and Winter M A, J. Clin. Microbiol, 1992, 30:3, 577-580). The authors suspended cells in a solution containing lysozyme and mutanolysin (two enzymes to form spheroplast) prior to their immobilization. However, a general non-enzymatic method to treat microorganisms with cell walls prior to their embedding in agarose gels has not been presented yet. Such method would be cheaper and simpler that current protocols in the preparation of samples.

Methods to isolate nuclei acids in solution, starting from cells heated in the presence of agents that provoke the permeability of the microorganism cell wall, were reported (European Patent 0,657,530, 1994, bulletin 95/24; U.S. Pat. No. 158,940, 1993). The method releases large fragments of undegraded nucleic acids from microorganisms without physically disrupting the entire cell wall. This method does not require lytic enzymes. However, intact DNA molecules are not obtained, because DNA is isolated in solution; and the authors did not propose the method to obtain the molecular karyotypes or the pulsetypes of the mentioned microorganisms. Authors reported that the obtained DNA is suitable for hybridization, but they did not address the possibility of DNA restriction with endonucleases. In conclusion, said method does not guarantee the obtaining of intact DNA molecules, whereas the possibility of digesting them with restriction enzymes remains unknown.

Therefore, a general procedure has not been proposed yet for the preparation of immobilized intact DNA from yeast, gram-positive and gram-negative bacteria and parasites by non-enzymatic methods in short times.

The preparation of immobilized DNA samples needs molds to form said samples. These molds can be reusable or disposable. The reusable molds should allow the sterilization. This is important for handling samples from pathogenic microorganism. The use of disposable molds requires continuous supply, which can be a limiting factor in laboratories with low budget.

Known molds are the following:
a) Molds that form independent and similar plugs (U.S. Pat. No. 4,473,452, Sep. 25, 1984);
b) Molds that form long ribbons, which are cut to form independent plugs;
c) Molds that form long square 'noodle' or long agarose rods, which are cut to form independent plugs (Birren B and Lai E. Pulsed Field Gel Electrophoresis: a practical guide, Academic Press, Inc. San Diego, Calif., 1993, pp 29-30).

In general, samples of dimensions larger than the gel slot are generated in said molds. For this reason, to obtain plugs with dimensions similar to the ones of slots, the ribbons, noodle, etc, need to be cut with a razor blade or another device. (CHEF Mapper XA Pulsed Field Electrophoresis System. Instruction Manual and Application Guide pp 40, Section 7. Catalog Numbers 170-3670 to 170-3673. Bio-Rad. 1995). However, cutting the ribbons or noodles provokes plugs of non-homogeneous sizes and dimensions, which influence the quality of the electrophoresis patterns. DNA molecule resolutions in the gel depend on the sample thickness. Consequently, the comparison of the patterns obtained in different lanes of the gel is difficult. Difficulties in the comparisons of band patterns represent a disadvantage in microorganism typing.

A mold for embedding cells in agarose gels and treat plugs was disclosed in the U.S. Pat. No. 5,457,050, Oct. 10, 1995. The mold could be disposable or reusable, depending on the material used to make it. It is claimed that the facility of the mold is that samples are formed and treated inside said mold. However, it is a disadvantage: if the plugs are kept inside the mold during the incubations, the time needed to obtain the samples suitable for PFGE analysis is notably lengthened. The effector molecules of the lysis and deproteinization solutions can poorly reach the target molecules inside the cells, because the contact area between the plugs and the incubation solutions is at least reduced to half.

Selection of the PFGE Experimental Conditions

The selection of the experimental conditions is complex. Methods to select the running PFGE conditions have been reported.

For example, the CHEF Mapper from Bio-Rad has an option of auto-algorithm and another one of interactive algorithm (CHEF Mapper XA Pulsed Field Electrophoresis System. Instruction Manual and Application Guide. pp 31-40 Catalog Numbers 170-3670 to 170-3673. Bio-Rad. 1995). Both options permit to calculate the pulse times, pulse ramp durations, reorientation angle, electric field and optimal running time to separate DNA molecules of a given sample. In contrast to the auto-algorithm, in which fixed experimental conditions are assumed, the buffer type, temperature and concentration, and the agarose type and concentration are permitted to vary as inputs in the interactive algorithm. Both algorithms work based on empirical and theoretical data collected during 5 years of experience (Bio-Rad Catalogue. Life Science Research Products. Bio-Rad Laboratories, pp185. 1998/99). However, the manufacturers recommend feed the auto-algorithm with DNA sizes smaller and larger than the expected sizes of the sample molecules. In addition, if extremely wide size ranges are entered to the auto-algorithm, as well as to the interactive program, erroneous results, such as band inversion in the mid range of the gel, can be generated.

Another empirical expression was proposed to give the electric pulse duration that separates the group of molecules of sizes falling between a given value and a higher one called RSL (Resolution Size Limit) (Smith D R. Methods I, 1990, 195-203). However, said expression is valid on specific experimental conditions alone, and it does not predict the resolution between two any molecules. Another function was proposed. It provides the approximate conditions of electric field and pulse time needed to separate a given group of molecules (Gunderson K and Chu G, Mol. Cell. Biol., 1991, 11:3348-3354). However, said function only permits to obtain rough estimates of the two mentioned variables, and does not provide the molecule migrations at any experimental condition.

Despite various theoretical studies were performed about DNA molecular reorientation during PFGE (Noolandi J, Adv. Electrophoresis, 1992, 5: 1-57; Maule J, Mol. Biotech. 1998, 9:107-126), said studies have not given a practical and useful result in the laboratories yet. They did not generate methods allowing the PFGE user to select and set the experimental conditions needed to separate the molecules under analysis.

The equations proposed by López-Cánovas et al. (López-Cánovas L et al., J. Chromatogr. A, 1998, 806:123-139) to describe DNA migration in PFGE, have not been used to predict the band patterns that should be obtained when varying the pulse time ramps, the electric field, temperature and running time. These variables are usually modified in microorganism typing.

PFGE Band Pattern Analysis

Computerized systems for image acquisition data from PFGE gels are available for band pattern analysis (Gerner-Smidt P et al., J. Clin. Microbiol, 1998, 37(3):876-877; Tenover F et al., J. Clin. Microbiol, 1995, 33(9):2233-2239; van Belkum A et al., J. Clin. Microbiol, 1998, 36(6):1653-1659). However, the comparison of the restriction patterns remains a subjective process, and it cannot be totally reduced to rigid algorithms (Tenover F et al., J. Clin. Microbiol, 1995, 33(9): 2233-2239). Although computer based analyses were performed, the final interpretation of the patterns must be subordinated to previous visual inspection.

Automatic and non-automatic band pattern analysis give as result the number of bands and the sizes of the molecules in the bands. It is usually done by comparing unknown DNA migrations with the migrations of molecular weight markers. However, PFGE is relatively new, and size markers for wide DNA size range are not always available. Consequently, the criteria used for bacterial typing, based on the interpretation of PFGE band patterns, consist in the determination of the number of different restriction fragments found when digesting the DNA of the microorganisms under comparison.

Equations to describe DNA molecule migrations under a single pulse ramp, different electric field strength and distinct temperature were proposed from electrophoresis data collected in experiments done in 1.5% agarose, Lachema and 0.5×TBE, 1×TBE: 89 mM Tris, 89 mM Boric Acid, 2 mM EDTA (López-Cánovas L et al., J. Chromatogr. A, 1998, 806:123-139). However, a method to extend and apply said equations to the analysis of band patterns after the application of pulse time ramps does not exist. The application of pulse time ramps is usually done in the comparative study of microorganisms.

Current Process for Microorganism Typing by PFGE

Total process for microorganism typing needs long time and many resources. Electrophoresis demands around 20 hours, methods of sample preparation, recommended by manufacturers or reported in the literature, require to use large amounts of enzymes (For instances, 80 mg/ml proteinase k) and long incubation times (CHEF Mapper XA Pulsed Field Electrophoresis System. Instruction Manual and Application Guide. pp 40-43 Catalog Numbers 170-3670 to 170-3673. Bio-Rad. 1995). A factor limiting the use of PFGE for microorganism typing is the time needed to complete the analysis of isolates, It is from 2 to 3 days, thus reducing the capacity of the laboratories to analyze many samples (Olive D M and Bean P, J. Clin. Microbiol, 1999, 37:6, 1661-1669).

DETAILED DESCRIPTION OF THE INVENTION

The present invention provides a process and a kit of reagents for typing isolates of microorganisms in a single working day (between 7 and 13 hours). Typing is done by the obtainment of the typical band patterns given by the separation of DNA molecules subjected to pulsed field gel electrophoresis in miniequipments. Specifically:

i) A method and the associated reagent kit to prepare, in 60 minutes at the most, intact DNA samples embedded in miniplugs of a gel, is provided herein. The method is based on the treatment of the cells with solutions that do not contain lytic enzymes. Said treatment can be done before or after the embedding of such cells in the gel. The cells may be yeast, parasites, gram-positive and gram-negative bacteria. Cells are embedded by means of a mold made of a flexible material that can be sterilized. It renders homogeneously sized miniplugs. The miniplug thickness varies from 0.03 to 0.1 cm depending on the mold dimensions used.

ii) Methods to predict lineal DNA migrations are provided. The methods are based on theoretical equations that permit the calculation of the migrations of lineal DNA molecules at any condition of electric field, temperature, pulse duration ramps and electrophoresis durations in the CHEF system. These methods permit to select the optimal electrophoresis condition to be applied to the gels, as well as to analyze the resulting band patterns obtained after performing the electrophoresis.

iii) Processes for the separation and analysis of DNA molecules of microorganisms are provided here. The separations are done in miniequipments for pulsed field gel electrophoresis. The miniCHEF miniequipments gives the band patterns in 2.5 to 5 hours and the MiniTAFE in 5 to 7 hours. The process permits to study up to 27 samples of immobilized DNA of microorganisms. Said samples are: a) prepared by the non-enzymatic procedure; b) separated in the minigels of miniequipments at the optimal electrophoresis conditions, conditions selected with the aid of the predictive methods, c) analyzed to estimate the sizes of DNA molecules. The estimations are performed with the aid of the methods of lineal DNA migration analysis, and are done for all DNA molecules loaded into the wells of the minigel and subjected to the action of two electrical fields in the miniequipments. Previously to the analysis, DNA molecules are detected in the gel by any staining procedure.

The method of sample preparation provided in this invention takes at the most 60 minutes, and it is simple and inexpensive, It neither require lytic enzymes nor proteases in the solutions to incubate microorganism cells and renders immobilized intact DNA. Intact DNA molecules can be digested with restriction enzymes and when they are subjected to pulsed field gel electrophoresis, intact DNA molecules or their restriction fragments migrate in the minigels forming band patterns corresponding to the molecular karyotypes or pulsetypes of the microorganisms.

The method is based on the chemical modification of the bacterial wall to allow the lysis of the microorganisms, or the diffusion of small effector molecules toward the target molecules in the cells. Undesired intracellular components are also eliminated during the preparation by dialysis. As results, intact DNA molecules are obtained in the miniplugs where the cells were embedded.

The method comprises the following general steps:
1) The cells of microorganisms are initially isolated from the fluids of hospitalized persons, or from a biotechnological collection or from the experiments done in a common laboratory of molecular biology, genetics or other.
2) The cells are grown in broth or on solid media of the proper composition for each microorganism.
3) The cells are collected by centrifugation and further washed.

4) The cells are a) embedded in the gel and incubated with the non-enzymatic solutions, or b) incubated with said solution(s) and further embedded in gel. In the case of 'a', the miniplugs containing immobilized cells are incubated first in the non-enzymatic solution for 5 to 30 minutes at 50° C. In the case of 'b', cells are incubated with the non-enzymatic solution for 5 to 30 minutes at 50° C. and later they are embedded in the agarose miniplugs.

5) Miniplugs containing the cells are dialyzed against the electrophoresis buffer, if the electrophoresis is going to be performed; or against the conservation buffer, if miniplugs are going to be stored; or against the restriction endonuclease buffer, if DNA molecules are going to be digested.

The organisms able to be incubated in the non-enzymatic solutions previous to the immobilization are *Saccharomyces cerevisiae*, *Hansenula polymorpha*, *Pichia pastoris* and *Staphylococcus aureus*. *Pseudomonas aeruginosa*, *Escherichia coli* and *Entamoeba histolytica* should be first immobilized and further incubated in the non-enzymatic solutions. The most effective washing solutions of cells are presented in Table I.

TABLE I

The most effective washing solutions of cells to prepare immobilized DNA.

| Harvested microorganisms | Washing solution composition |
|---|---|
| Yeast | 0.05 M EDTA, pH 7.5 |
| *Entamoeba histolytica* | PBS, pH 7.4 |
| *Pseudomonas aeruginosa* | 0.15 M NaCl |
| *Staphylococcus aureus*, *Escherichia coli* | 0.15 M NaCl, 0.01 M EDTA, pH 8.0 |

Non enzymatic solutions to incubate the cells, or the miniplugs containing cells, have anionic detergents, a metal chelating agent, an agent able to compete for hydrogen bond formation and Tris buffer. The most efficient contains: 1% sarkosyl, 0.1 M EDTA, 0.01 M Tris-base, 4M Urea and its pH is 9.5 (NDSU). To incubate cells of gram-positive and gram-negative bacteria nonidet P-40 is added (NDSUPlus).

Some microorganisms, e.g. *Escherichia coli*, should be incubated first for 10 minutes at 37° C. in a non-enzymatic lysis solution. It contains 1% sarkosyl, 1% nonidet P-40, 0.1 M EDTA, 0.01 M Tris base, and its pH is 8.0. Further, they are incubated for half an hour in the NDSUPlus solution.

The storage buffer of the miniplugs containing immobilized DNA is TE-100 (0.01M Tris-base, 0.1 M EDTA, pH 8.0).

The procedure to embed cells in agarose miniplugs consists in using a mold made of flexible material that can be sterilized. The mold is a sheet of silicone, rubber or other flexible material of up to 0.5 cm wide (see in Examples, example 1). Several square depressions are stamped in the sheet. Depression may be up to 0.3 cm wide and 0.03 to 0.1 cm depth. To pour the agarose-cell suspension, the mold is pre-warmed at 42° C. by putting it on a surface heated at this temperature, afterwards the suspension is poured onto the mold, and evenly distributed in the depressions with the aid of a spatula. Then, the mould is covered with a lid (It can be made of glass, acrylic, plastic or any other material) and incubated between 4-15° C. until the miniplugs are harden. The homogeneously sized miniplugs are extracted from the flexible mould by holding its perimeter sides and bending the mold inside of a recipient that contains the non enzymatic solution for miniplug treatment. The suspension is prepared in such a way that 0.12 to $3 \times 10^8$ bacterial cells, $8 \times 10^7$ yeast cells or $6 \times 10^4$ trophozoites of *Entamoeba histolytica* are embedded per each miniplug of $0.3 \times 0.07$ cm of dimension. All mentioned microorganisms can be prepared by using this type of mold. Altogether, this type of mold can be used to prepare miniplugs that contain any other type of cells.

In the present invention, the method to select the optimal electrophoresis conditions to be applied in the miniequipments is based on calculating the migrations of lineal DNA molecules. The calculation is done by using a group of theoretical equations that describe the migration, the reorientation times and the migration velocities of lineal DNA molecules in the miniCHEF minigel. The equations are fed with the values of electric field and temperature and they should be comprised between 1-20 V/cm and 4-30° C., respectively. To apply the equations, the electrophoresis is assumed to be done in 1.5% agarose and the electrophoresis buffer should be 44.5 mM Tris, 44.5 mM Boric acid, 1 mM EDTA, pH 8.3 (TBE 0.5×). The theoretical equations that describe DNA migration are the following:

$$D = \sum_{r=1}^{n} \{vr \, tp_r *_r (tp_r - tr) Np_r + vm(tp_r - tr)[1 - *_r(tp_r - tr)]Np_r\} \quad \text{Eq. 1}$$

$$vr = 0.0207[QE^{1.45}/(8\Sigma KL^{1.35})] \quad \text{Eq. 2}$$

$$vm = 0.665[QE^{1.76}/(8\Sigma KL^{1.08})] \quad \text{Eq. 3}$$

$$tr = 0.134(L^{1.14}/vr)^{0.926} \quad \text{Eq. 4}$$

$$*_r(tp_r - tr) = 1 \text{ if } (tp_r - tr) \delta 0 \text{ and } *_r(tp_r - tr) = 0 \text{ if } (tp_r - tr) > 0 \quad \text{Eq. 5}$$

where:
tr: reorientation time (s),
vr: migration velocity during reorientation (cm/s),
vm: migration velocity after reorientation (cm/s),
Q: $1e^- \times bp$ (DNA net charge, $e^-$: electron charge in statcoulomb),
L: $0.34 \text{ nm} \times bp$ (DNA contour length, in cm),
E: electric field strength in statvolts/cm,
K: viscosity of the buffer solution in Poises, and K was calculated by interpolating the experimental temperature (° C.) in a polynomial function that relates water viscosity with temperature.
D: total migration of a DNA molecule in the minigel of CHEF (cm),
d: migration per pulse (cm),
n: number of pulse time ramps.
$Np_r$: number of pulses in the ramp 'r',
$tp_r$: pulse duration in the ramp 'r' (s), The method to select the optimal electrophoresis conditions includes the following steps:

I. Calculate the duration of the pulses ($tp_r$) that will be used in the ramps. To perform it:
 1) The equations are fed with the selected values of electric field and temperature. The sizes of the smallest and largest linear DNA molecules should be given also.
 2) By means of the use of equation 4, the reorientation times of smallest and largest linear DNA molecules are estimated.
 3) The mean of both reorientation times (a single $tp_r$, or $tp_1$) is calculated if DNA molecules of sizes comprised between the largest and the smallest molecules are wished to be included in a single pattern.
 4) A numerical sequence of pulse duration's is calculated ($tp_r$). It begins with pulse duration that is 1.5 times lower than the reorientation time of the smallest molecule, and ends with 1.5 times greater than the reorientation time of the largest molecule. Linear increments in the pulse duration are used in the numerical sequence of calculated $tp_r$.

5) To carry out the electrophoresis the tp calculated in the step (3) could be taken, otherwise, the numeric sequence of $tp_r$, calculated in step (4), is used.

II. Calculate the total run time. The total electrophoresis run time is estimated on the basis of the calculation of the migration of the smallest linear DNA molecule. This is performed as follows:
  1) Equations 2 and 3 are fed with the values of electric field and the temperature of the electrophoresis buffer.
  2) The reorientation time and the migration velocities of the smallest molecule are estimated. Equation 1 is fed with the durations of the electric pulses ($tp_r$) estimated in step I. The initial values of the number of pulses are fixed.
  3) The number of pulses of each ramp 'r' is increased one by one, and each time the migration of the smallest molecule is estimated by means of the use of equations 1 and 5. The iterations are repeated until the molecule reaches the position that is 0.1 to 1 cm far apart from the bottom of the minigel III. By means of using equations 1-5, the migrations of the molecules, wished to be separated, are calculated for the 'n' ramps, and then, the band patterns given by these molecules in the minigels of miniCHEF are predicted for the conditions selected for electric field, temperature, number of ramps 'r', duration of electric pulses and number of pulses ($Np_r$). This calculation includes the following steps:
  1) It is assumed that the electrophoresis is performed in 1.5% agarose gel and 0.5×TBE buffer.
  2) The values of electric field and buffer temperature (that will be used in real experiment), are defined to the equations 2 and 3.
  3) According to the values estimated in the previous steps, the total number of ramps (n), the number of pulses that will be applied in each ramp ($Np_r$) and the duration of the pulses in each ramp ($tp_r$) are defined to the equation 1.
  4) The sizes of the molecules, to be analyzed, are specified.
  5) By means of the use of the equations 1-5, the distances that should migrate the DNA molecules (wished to be analyzed) are calculated for the specified electrophoresis conditions.
  6) The migrations, calculated for the linear DNA molecules, are presented in a numerical or graphical format.
  7) The steps 2-6 are repeated until the predicted pattern shows the optimal separation among the linear DNA molecules.

IV. Based on the above results, the experimental condition that render the optimal separation between the linear DNA molecules is selected. Then, the power supply, the electrophoresis control unit and the cooling system are fed with these data.

The preferred mean of implementing this method could be a computer program that would facilitate the simulation of the separation of DNA molecules of different sizes in miniCHEF. This program would calculate the optimal experimental conditions for DNA separations. The program would also provide a rapid mean to perform the required calculations for implementing this part of the present invention.

A program was created to simulate the band pattern. The program permits the user to vary the following variables:
  1—The size of the DNA fragments or the intact DNA molecules wished to be separated in the gel.
  2—The buffer temperature.
  3—The voltage.
  4—The pulse time and the number of electric pulses applied in each ramp.
  5—The number of pulse time ramps. It is comprised between 1 and 1000 ramps.

Fed with the mentioned values, the program provides the following results:
  1—DNA molecule velocities (in cm/s) during and after DNA reorientation.
  2—The reorientation time of each DNA molecule (in seconds).
  3—The migration of each molecule in the gel for the selected run duration.
  4—The migration of each molecule and the scheme of the electrophoresis pattern.

The graphical representation of the distances that linear DNA molecules should migrate under the specified electrophoresis conditions is done as follows:
  i) Drawing a minigel with the same dimensions of the real minigel, and drawing the wells where the samples are hypothetically loaded.
  ii) Placing lines under each well. They would represent the bands formed by DNA molecules of different sizes after the separation. Each line has the width of the well. These lines are drawn separated from the wells the distances that DNA molecules would migrate in the real minigel.
  iii) Assigning to each line, or hypothetical band, a color. The color varies with the size of the molecules that the band contains. That's, using a color code that identifies the molecules of a given size.

This program constitutes a method to choose the proper experimental conditions to separate intact chromosome-sized DNA molecules or large DNA fragments by Pulsed Field Gel Electrophoresis in the miniCHEF. If the program is fed with distinct values of the experimental variables, different electrophoresis patterns are obtained, thus permitting the identification of the experimental conditions that should separate the molecules of interest in CHEF and miniCHEF. This approach does not spend reagents or biological samples. It is based on the theoretical equations that describe linear DNA migration in miniCHEF. Said equations were fitted using migration data of linear DNA, obtained in real miniCHEF experiments. Therefore, they describe correctly the migration of said molecules when they are subjected to electrophoresis. In addition, they do not render anomalous results of mobility inversion in the center of the gel.

In the present invention, the rapid microorganism typing is proposed by means of the electrophoretic separation of DNA in the miniequipments miniCHEF and miniTAFE. Samples of *Saccharomyces cerevisiae, Hansenula polymorpha, Pichia pastoris, Pseudomonas aeruginosa, Escherichia coli, Staphylococcus aureus* and *Entamoeba histolytica* cells, prepared using the non-enzymatic procedure, are loaded in the minigels. Samples of these or any other microorganisms, prepared by the conventional enzymatic procedures, can also be loaded.

MiniCHEF and miniTAFE minichambers are used to obtain the karyotypes, or pulsetypes. The distances between the pairs of electrodes with opposite polarity are around 11.6 cm and 7.8 cm in miniCHEF and MiniTAFE, respectively. Electric field intensity up to 20 V/cm can be applied in miniCHEF and 22 V/cm in miniTAFE.

The electrophoresis equipments, selected to carry out this part of the invention, include the miniCHEF and miniTAFE minichambers previously described by Riverón et al. 1995 (Riverón A M et al., Anal. Lett., 1995, 28:1973-1991; European Patent Application EP 0,745,844, Bull. 1996/49; U.S. patent application Ser. No. 08/688,607, 1995; Cuban patent RPI Nro. 02/95, 1995), the disclosure of which is totally incorporated herein by reference. The floor of the miniCHEF chamber was slightly modified to support an agarose minigel from 4 to 7 cm wide. In the minigel, 12 to 27 samples can be loaded. The miniTAFE chamber was slightly widened to support a minigel of 7 cm wide. In miniTAFE minigel, 27 samples can be loaded.

The agarose concentration of the minigel can vary from 0.8 to 1.5%, being the preferred value 1.5%. The 1×TBE buffer is 0.089 M Tris base, 0.089 M boric acid and 0.002 M EDTA (sodium salt of ethylenediamine tetra acetic acid) and it can be used in concentrations ranging form 0.25 to 1×, but preferably 0.5×. The buffer temperature can vary between 4 and 30° C. The 1×TAE buffer (0.04 M Tris-Acetate and 0.001 M EDTA) can also be used. To clamp the voltage in the miniCHEF electrodes, and alternate the electric field orientation in miniCHEF and miniTAFE chambers any purposely-constructed device can be used, including the equipment described by Riverón A M et al., Anal. Lett, 1995, 28(5):845-860; and Riverón A M et al., Anal. Lett., 1995, 28(11):1973-1991.

To energize the electrodes, any power supply with maximum output of 300 watts can be used.

Agarose miniplugs are loaded into the wells of the minigel. The wells are formed by the teeth of the comb used to cast the minigel. Different combs can be used to load wider or narrower miniplugs. It depends on the dimensions of the miniplugs that were cast.

Ethidium bromide is used to stain the molecules present in each band of the minigel. The minigel is illuminated with ultraviolet light (UV transilluminator) and the images are taken with a camera using a filter of 550 nm. Any other staining procedure can be used also.

The electric field strength, buffer temperature, pulse time ramps, electrophoresis time and number of electric pulses set in each ramp come from the results of the simulator (or the method for selecting the optimal conditions to separate the molecules), or from the results of another method that the user employs, including his empirical experience. When the simulator is used, the concentration of the buffer should be 0.5× TBE, the agarose (Lachema) gel must be 1.5%, the electric field must be up to 20 V/cm, the temperature must be between 4 and 30° C. and the chamber must be the miniCHEF. When the simulator is employed, but the use of miniTAFE is wished, the same conditions of electric field and temperature, given by the simulator, can be used, but the number of pulses of each ramp should be increased in 1.5 times and the duration of the pulses in 1.2 times.

Under other conditions of electric field strength and temperature, the typical band patterns of the molecules contained in the sample that is going to be separated can be obtained also in the miniequipments.

In the present invention the preferred method to analyze the band patterns obtained after the electrophoresis is based on measuring distances migrated by linear DNA molecules in the minigel, and the use of equations 1-5 to calculate the sizes of the molecules. The method requires that the band patterns were obtained in the minigels by electrophoresis in the miniCHEF equipment at an electric field comprised between 1 and 20 V/cm, temperature between 4 and 30° C., 1.5% agarose (Lachema), 0.5×TBE buffer and any number 'n' of pulse time ramps (comprised between 1-1000) and electrophoresis time. The method consists in:

i) Measuring the distances migrated by linear DNA molecules in the minigels after the electrophoresis and the staining of the bands in the minigels.

ii) Feeding the equations 1-5 with the values of electric field, buffer temperature, number of ramps (n), number of pulses applied in each ramp ($Np_r$) and the duration of the pulse in each ramp ($tp_r$).

iii) Feeding the program with the real distances (D in cm) migrated by the bands after the electrophoresis.

iv) Calculating the size of the molecules of each band from the migrated distances. It is done according to:

1) A hypothetical DNA molecule of an initial size of 1000 pairs of bases is defined.

2) Equations 2, 3 and 4 are used to estimate vr, vm and tr, respectively, of the hypothetical DNA molecule.

3) By means of the use of the equations 1 and 5, the theoretical migration (Dt in cm) of the hypothetical DNA molecule is estimated for the electrophoresis conditions used in the experiment.

4) D and Dt are compared. If Dt is greater than D, the size of the hypothetical molecule is increased in 1000 bp.

5) Steps 2) to 4) are repeated until the migration estimated for the hypothetical DNA molecule is lower or equal than the distance (D) migrated by the real molecule in the minigel.

6) The DNA molecules in the band are assumed to have a size equivalent to the size of the hypothetical DNA molecule that accomplishes the condition proposed in 4). The tr, vr, and vm values estimated for the hypothetical molecule are also assumed to be the ones of the real molecule.

7) Steps 1) to 6) are repeated with the distances measured for all bands; that is for all molecules separated in the minigel.

The description of the electrophoresis can be given by the electrophoresis pattern and by a matrix. It contains the ordinal of each fragment or separated molecule in the rows; whereas in the columns are the sizes, reorientation times and migration velocities of the separated molecules.

A computer program may provide the preferred method of practicing this part of the present invention. Such program would provide a rapid means of performing the calculations to estimate the size and the kinetic parameters of the fragments or intact DNA molecules separated in the electrophoresis. A program was created that permits the user to change the following variables:

1—The migrated distances of the molecules, that is the position of each band of the pattern in the gel.

2—The buffer temperature.

3—The voltage set in the electrophoresis chamber.

4—The pulse time and the number of electric pulses set in each ramp.

5—The number of ramps (limited between 1-1000)

Feeding the program with the mentioned values, it provides the following results:

1—DNA velocities (cm/s) during and after reorientation.

2—The reorientation times (s) of each molecule.

3—The size of the molecules in kilobases (kb).

Feeding the program with the electrophoresis conditions in the miniCHEF and the resulting migrated distances of the molecules, the program can calculate the sizes and the kinetic parameters of the molecules present in each band of the gel. In general, molecular weight markers are not needed to identify the molecules of the bands. This analysis will permit the classification of the DNA fragments or the molecules according to their kinetic properties. The results of the electrophoresis can be also described with the aid of another method usually employed.

EXAMPLES

Example 1

Mold Able to be Sterilized for the Preparation of Sample Miniplugs

An example of the mold able to be sterilized and made of a flexible material (silicone, rubber or any other material) is shown in the scheme of FIG. 1. The mold is used to prepare agarose-embedded DNA samples. The sheet (1) has 49 depressions (2). The agarose-cell suspension is poured onto the mold or sheet and distributed in the mold with the especial spatula (4). Later, the sheet (1) is cover up with the lid (3), generating the miniplugs (5) containing embedded cells. The sheet of the real mold was made with melted silicone. It was poured into another mold until the sheet (1) was formed. In the example, miniplug dimensions are 3×3×0.7 mm (length, width×thickness). To recover the miniplugs (5) from the sheet (1), said sheet is held by its ends and bent inside a container with a solution. Consequently, the miniplugs are released from the sheet and dropped into the solution.

In other mold variants, the depression width may vary from 1.5 mm to the minigel width, whereas the thickness can vary from 0.5 mm to 1.5 mm. The number of depressions stamped on the sheet can also vary.

Example 2

Non-enzymatic Preparation of Agarose-embedded Intact Yeast DNA Starting from Cells Cultured in Broth Media

Yeasts (*S. cerevisiae*, *H. polymorpha* or *P. pastoris*) were grown in liquid YPG medium (YPG: 10 g yeast extract, 20 g glucose and 10 g peptone dissolved in one liter of distilled water) with shaking at 30° C. until late log phase. Cells were harvested by centrifugation and washed with 0.05 M EDTA, pH 7.5 (washing solution, Table I). Agarose-embedded intact DNA is obtained performing any of the two following variants:

Variant 1: Cells are incubated prior to their embedding in agarose miniplugs.

Variant 2: Cells are embedded in agarose miniplugs and further the miniplugs are incubated.

In both variants the cells are embedded in agarose by preparing a cell suspension of $1.3 \times 10^{10}$ cell/ml in 1.5% low melting agarose which was first dissolved in 0.125 M EDTA. The cell suspension is poured onto the sheets (1) of the mold shown in FIG. 1, then, the mold is covered with the lid (3) and the agarose is let harden until the sample miniplugs (5) are formed.

In the variant 1, the cellular pellet obtained from 100 ml of broth culture is resuspended in 5 ml of NDSU and incubated for 5 minutes at 50° C. Further, the suspension is diluted fivefold in TE-100. The cells are collected by centrifugation and embedded in agarose miniplugs as it was above described.

In the variant 2, the cells are harvested, washed and further embedded in agarose miniplugs (see Table I). Agarose miniplugs with cells are incubated in NDSU for half an hour at 45° C.

Miniplugs are washed twice for 5 minutes in TE-100 (0.01 M Tris-base, 0.1 M EDTA, pH 8.0) and further stored in fresh TE-100 at 4° C. After miniplug treatments by any of the two variants and prior to electrophoresis, the miniplugs are incubated in TBE for 10 minutes at run temperature.

The photograph of the minigel (10) where the *S. cerevisiae* chromosomal (12) and mitochondrial (13) DNA were separated in band patterns is shown in FIG. 2. Samples were prepared embedding the cells in miniplugs and incubating them in NDSU (variant 2). The minigel of 7 cm wide, which permits a maximum of 27 samples (11), was used in the miniCHEF. Running electrophoresis conditions were 10 V/cm, 20° C., 1.5% agarose, 0.5×TBE, 50 seconds of pulse time and 4 hours of electrophoresis.

The photograph of the lane (16) of a miniCHEF minigel in which the *H. polymorpha* chromosomal (17) and mitochondrial (18) DNA were separated in band patterns is also shown in FIG. 2. The chromosomes of *H. polymorpha* were prepared according to variant 2. They were separated in the miniCHEF at 10 V/cm, 20° C., 1.5% agarose, 0.5×TBE, 120 seconds of pulse time and 4 hours of electrophoresis.

*S. cerevisiae* chromosomes were also separated in the miniTAFE minigel (20) shown in FIG. 2. Chromosomal (21) and mitochondrial (22) DNA band patterns are also shown. The samples were prepared using the variant 1, that's, incubating the cells prior to their embedding in agarose. Said samples were loaded in the 13 slots (23) formed by the comb. The minigel is 7 cm wide. In the miniTAFE were applied 10 V/cm, 20° C., 1.5% agarose, 0.5×TBE, 60 seconds of pulse time and 6 hours of electrophoresis.

Example 3

**Non-enzymatic Preparation of Agarose-embedded Intact DNA from *Pseudomonas Aeruginosa* Grew in Broth and on Solid Media**

Two colonies of *P. aeruginosa* were isolated from a blood-agar plate. One of them was inoculated in 5 ml of LB medium (10 g yeast extract, 5 g sodium chloride and 10 g bacto-triptone per liter of distilled water) and the other was streaked on a LB plate (LB plus 1.2% bacteriologic agar).

Both cultures were incubated overnight at 37° C. Broth culture was incubated with shaking and the plates were kept static. Cells, grown in broth, were collected by centrifugation, whereas the plates were washed with the proper washing solution (shown in Table I) and further collected by centrifugation.

Cells grew in broth or solid media were washed with the solution shown in Table I, collected by centrifugation and re-suspended at a concentration of $2 \times 10^9$ cells per milliliter of 1.5% low melting agarose dissolved in 0.15 M NaCl. Agarose-cells mix was poured onto the sheet (1) of the mold shown in FIG. 1, further, the sheet was cover with the lid (3) and the agarose was let to set until the plugs (5) were formed. Miniplugs were incubated with NDSUPlus for half an hour at 50° C. Later, miniplugs were washed twice for 10 minutes in TE-100 at 50° C. and stored in fresh TE-100 at 4° C. Prior to restriction enzyme digestion, miniplugs were washed and incubated for 10 minutes in Xba I restriction enzyme buffer. Each miniplug was digested with 20 U of Xba I for 2 hours at 37° C. Restriction fragments were separated in the miniCHEF at 10 V/cm, 20° C., 1.5% agarose and 0.5×TBE, applying a pulse ramp of 20, 15, 10, 5 and 3 seconds and 5, 15, 320, 1020 and 100 pulses, respectively.

The band patterns (26) separated in the miniCHEF minigel (25) are shown in the FIG. 3. *P. aeruginosa* miniplugs (27) were prepared from cultures in liquid LB media, whereas the miniplugs (28) were prepared from cultures done on LB plates. The sizes of the DNA fragments separated are also shown in the figure.

Example 4

**Non-enzymatic Preparation of Agarose-embedded Intact DNA from *Staphylococcus Aureus* Grew on Solid Media**

A colony of *S. aureus* was isolated from blood-agar medium and streaked on a Mueller-Hinton plate (Oxoid). The plate was incubated overnight at 37° C. The plate surface was washed with washing solution (0.15 M NaCl, 0.01 M EDTA, pH 8.0, Table I) and the cells were collected by centrifugation.

Agarose-embedded intact DNA was prepared performing any of the two following variants:
Variant 1: Cells are incubated prior to their embedding in agarose miniplugs.
Variant 2: Cells are embedded in agarose miniplugs and further, the miniplugs are incubated.

In both variants the cells were embedded in agarose by preparing a cell suspension at a concentration of $4 \times 10^{10}$ cell/ml in 1.5% low melting agarose dissolved in washing solution (Table I). The cell suspension was poured onto the sheet (1) of the mold shown in FIG. 1, further the sheet was covered with the lid (3) and the agarose was let harden until the miniplugs (5) were formed.

In the variant 1, the cellular pellet was resuspended in 3 ml of NDSUPlus and incubated for 30 minutes at 50° C. After that, the suspension was diluted fivefold in TE-100. The cells were collected by centrifugation and embedded in agarose miniplugs.

In the variant 2, cells were harvested, washed and further embedded in agarose miniplugs. Agarose miniplugs were incubated with NDSUPlus for one hour at 50° C.

After the treatments by any of the two variants the miniplugs were washed twice for 10 minutes each in TE-100 at 50° C. Prior to restriction enzyme digestion, miniplugs were washed and incubated with Sma I restriction enzyme buffer for 10 minutes resting on ice. Each miniplug was digested with 20 U of Sma I for 2 hours at 37° C. *S. aureus* DNA macrorestriction fragments, separated in the band pattern (31) in the minigel (30), are shown in the FIG. 4. Miniplugs (32) were prepared according to variant 2, whereas the ones (33) by the variant 1. Running conditions were 10 V/cm, 20° C., 1.5% agarose, 0.5×TBE and pulse ramps of 1, 5, 9, 13, 17 and 21 seconds. In all ramps, 130 pulses were applied. The sizes of the DNA fragments separated are also shown in the figure.

Example 5

**Non-enzymatic Preparation of Agarose-embedded Intact DNA from *Entamoeba Histolytica***

*E. histolytica* (clone A) trophozoites were grown in TYI-S-33 medium to log phase. Trophozoites were harvested by chilling the culture flasks and pelleting the cells by centrifugation. The pellet was washed with cold PBS and incubated with cold hypertonic solution (0.5 M NaCl, 0.05 M EDTA, 0.01 M Tris, pH 7.0) for 15 minutes at a ratio of $2.5 \times 10^6$ trophozoites per milliliter of solution. Further, $10^8$ trophozoites were resuspended in one milliliter of 2% low melting agarose in hypertonic solution. Suspension was poured onto the flexible silicone mold shown in FIG. 1 and miniplugs were allowed to harden at 4° C. Miniplugs were incubated with NDSU (0.01 M Tris-base, 0.1 M EDTA, 1% sarkosyl (w/v), 4 M urea, pH 9.5) at 45° C. for one hour. Before the electrophoresis, the miniplugs were incubated with 0.5×TBE for 10 minutes at run temperature. To store the miniplugs, they were washed with TE-100 (0.01 M Tris-base, 0.1 M EDTA, pH 8.0) twice for 5 minutes each time and stored in fresh TE-100 at 4° C.

DNA band patterns (36) of *E. histolytica* (38), *S. cerevisiae* (37) and lambda-DNA mers (39) are shown in FIG. 5. Electrophoresis was performed at 9.03 V/cm electric field, 120 seconds of pulse time, 20° C., 1% agarosa (Seakem), 0.5× TBE running buffer and 6 hours of electrophoresis. Miniplugs of 0.1 cm thickness were loaded.

Example 6

Design of the Electrophoresis Running Conditions in the MiniCHEF. Setting the Experimental Conditions by Using the Simulator (Method for Selecting the Optimal Conditions for DNA Separation)

The pulse time ramps needed to separate the *S. cerevisiae* chromosomes in the miniCHEF chamber of 11.6 cm between the electrodes of opposite polarities were simulated. The purpose was to obtain the pattern that displays the 11 bands formed by all *S. cerevisiae* chromosomes. The electrophoresis was assumed to be performed in 1.5% agarose gel and 0.5×TBE as running buffer. The size values of *S. cerevisiae* chromosomes reported by Goffeau were taken (Goffeau A et al., Science, 1996, 274: 546): 230 kb (chrom. I), 270 kb (chrom. VI), 315 kb (chrom. III), 440 kb (chrom. IX), 589 kb (chrom. VIII), 577 kb (chrom. V), 667 kb (chrom. XI), 745 kb (chrom. X), 784 kb (chrom. XIV), 813 kb (chrom. II), 924 kb (chrom. XIII), 948 kb (chrom. XVI), 1091 kb (chrom. VII and chrom. XV), 1554 kb (chrom. IV) and 2352 kb (chrom. XII).

The simulator predicted four pulse time ramps of 5, 40, 75 and 110 s of pulse times and 42 pulses in each ramp to achieve the optimal separation of *S. cerevisiae* chromosomes in a single pattern for 10 V/cm electric field strength and 20° C. The results of migration, reorientation times, migration velocities and the color code used to identify each chromosome are shown in Table II.

TABLE II

Quantitative results obtained using the simulator. Sizes (kb) and colors assigned to the *S. cerevisiae* chromosomes according to the color code of the simulator.

| Size of the *S. cerevisiae* chromosomes (kb) | Color code | tr (s) | vr × 10$^5$ (cm/s) | vm × 10$^4$ (cm/s) | D predicted by simulator (cm) | D experimental (cm) |
|---|---|---|---|---|---|---|
| 250 | blue | 4.9 | 8.8843 | 2.7462 | 2.45 | 2.67 |
| 270 | green | 5.5 | 8.6482 | 2.7293 | 2.40 | 2.67 |
| 315 | red | 6.8 | 8.1940 | 2.6959 | 2.28 | 2.46 |
| 440 | cyan | 10.8 | 7.2894 | 2.6247 | 1.95 | 2.22 |

TABLE II-continued

Quantitative results obtained using the simulator. Sizes (kb) and colors assigned to the *S. cerevisiae* chromosomes according to the color code of the simulator.

| Size of the *S. cerevisiae* chromosomes (kb) | Color code | tr (s) | vr × 10⁵ (cm/s) | vm × 10⁴ (cm/s) | D predicted by simulator (cm) | D experimental (cm) |
|---|---|---|---|---|---|---|
| 577 | magenta | 15.6 | 6.6297 | 2.5684 | 1.59 | 1.85 |
| 589 | dark gray | 16.1 | 6.5821 | 2.5642 | 1.57 | 1.85 |
| 667 | brown | 19.1 | 6.3017 | 2.5388 | 1.42 | 1.66 |
| 745 | light blue | 22.2 | 6.0625 | 2.5165 | 1.27 | 1.49 |
| 784 | light green | 23.9 | 5.9551 | 2.5062 | 1.19 | 1.35 |
| 813 | light red | 25.1 | 5.8799 | 2.4989 | 1.13 | 1.18 |
| 924 | light cyan | 29.9 | 5.6223 | 2.4735 | 0.92 | 0.92 |
| 948 | light magenta | 31.0 | 5.5721 | 2.4684 | 0.89 | 0.92 |
| 1091 | white | 37.6 | 5.3047 | 2.4408 | 0.73 | 0.6 |
| 1554 | black | 61.3 | 4.6870 | 2.3727 | 0.52 | 0.4 |
| 2352 | blue | 108.6 | 4.0542 | 2.2953 | 0.46 | 0.17 |

D experimental: Distance migrated by the molecules in the minigel (40) of FIG. 6.
D predicted: Distance migrated by the molecules according to the simulator predictions for the running conditions used in the experiment of FIG. 6.
vr: migration velocity of the molecules during reorientation.
vm: migration velocity of the molecules after reorientation.
tr: reorientation time of the molecules.

The photograph of the real minigel (40) with the band patterns of the chromosomes of *S. cerevisiae* 196-2 (41) obtained in the miniCHEF at the conditions predicted by simulator is shown in FIG. 6. The band pattern simulated in the hypothetical minigel (42) and drawn by the simulator is also shown. Both patterns are similar. Agarose-embedded intact DNA molecules from *S. cerevisiae* 196-2 separated in the real experiment were prepared according to the non-enzymatic procedure disclosed in this invention.

The flow chart of a part of the simulator disclosed in this invention is shown in FIG. 7. The method of calculations to estimate the pulse ramps, based on migration data or previously known size data, is shown in the flow chart.

When the user feeds the method with migration data, the simulator initially estimates the sizes of the molecules from said data and further it estimates the set of lineal pulse time ramps. When the user feeds the method with size data, the simulator directly estimates the pulse time ramps. The criterion to finish the increments in the number of pulses is the number of pulses that provokes the smallest molecule to migrate 2.5 cm.

Finally, the simulator provides the result that the user should observe in the gel (see the real band patterns in minigel 43 and the simulated in the hypothetical minigel 42 of FIG. 6) for the pulse ramps calculated by the program and applied to the group of molecules specified by the user. The program also gives quantitative data. This part of the diagram is not shown because the solution is trivial.

Example 7

Analysis of the Electrophoresis Karyotypes or Pulsetypes

The electrophoresis karyotype (61) of *S. cerevisiae*, obtained in the miniCHEF after the separation of said chromosomes in 1.5% agarose, 0.5×TBE, 10 V/cm, 20° C., 2.95 seconds and 453 pulses and 21.56 seconds and 453 pulses, is shown in FIG. 8. The migration of each band (62-66) was measured in said karyotype.

The method for analyzing the migrations was fed with the migration datum of each band, the electric field strength, the duration and number of pulses and the temperature of the running buffer.

The method disclosed herein allowed the calculation of the size, reorientation times and migration velocities of the molecules separated in each band. These results are shown in Table III. This is the type of result given by the procedure for analyzing the migrations disclosed in this part of the invention.

TABLE III

Size, reorientation time and migration velocities of the molecules in each band. Estimations were done by feeding the method with the position of each band in the gel, after the application of the pulse ramps.

| | 10 V/cm, 20° C. 2.95 s/453 pulses; 21.56 s/453 pulses | | Real | Estimations | | |
|---|---|---|---|---|---|---|
| Bands | D exp | D theor | size (kb) | Size (kb) | vr × 10³ cm | vm × 10³ cm | tr (s) |
| 62 | 2.36 | 2.23 | 230 | 210 | 0.09443 | 0.2785 | 3.9 |
| 63 | 2.29 | 2.14 | 270 | 226 | 0.09204 | 0.2768 | 4.3 |
| 64 | 1.97 | 1.96 | 315 | 302 | 0.08310 | 0.2705 | 6.4 |
| 65 | 1.55 | 1.42 | 440 | 401 | 0.07530 | 0.2644 | 9.5 |
| 66 | 0.84 | 0.82 | 577 | 564 | 0.06683 | 0.2573 | 15.2 |

D exp: Distance migrated by the molecule in the minigel of FIG. 8.
D theor: Distance that real molecule of each size should migrate at the running conditions of the experiment FIG. 8.
vr: migration velocity of the molecule during reorientation.
vm: migration velocity of the molecule after reorientation.
tr: reorientation time.

The flow chart of the method for the analysis of DNA migrations is shown in FIG. 9. The diagram was drawn to process a molecule of a single size, but the steps are repeated for all analyzed molecules.

When the method described in the example 7 is fed with migration data, said method estimates the sizes of the molecules as the method described in this example does.

Example 8

MiniCHEF Typing of *Escherichia Coli* Isolates

A single colony of each isolate (INN3 and INN7), characterized at phenotypic level as *Escherichia coli*, was taken from blood-agar plates. Further, they were sub-cultured in 5 ml of LB medium (10 g of yeast extract, 5 g of sodium chloride, 10 g of bacto-triptone per liter of distilled water). Each culture was incubated overnight at 37° C. with shaking.

Cells from each culture were washed (see washing solution in Table I), centrifuged and the pellet re-suspended to a ratio of $2 \times 10^9$ cell per milliliter in 1.5% low melting point agarose dissolved in 0.15 M NaCl. Each agarose-cell mix was poured onto the sheet (1) of the mold shown in FIG. 1. The sheet was covered with the lid (3) and the agarose was let harden until the miniplugs were formed (5). Both groups of miniplugs were incubated with NDSUPlus for half an hour at 50° C. Later, the miniplugs were washed and incubated for 10 minutes with Xba I restriction enzyme digestion buffer and each one was digested with 20 U of Xba I for 2 hours at 37° C.

Band patterns (87) separated in the minigel (86) of the miniCHEF are shown in FIG. 10. The separations achieved in the miniCHEF of the Xba l-digested total DNA from INN3 (88) and INN7 (89) *E. coli* isolates permitted to identify six common fragments between them (90). Then, according to Tenover (Tenover F et al., J. Clin. Microbiol., 1995, 33:9, 2233-2239) they were classified as two different *E. coli* subtypes. DNA restriction fragments were separated in the miniCHEF at 10 V/cm, 20° C., 1.5% agarose and 0.5×TBE, applying pulse ramps of 25, 20, 15, and 5 seconds and 35, 40, 50, 140 and 800 pulses, respectively.

ADVANTAGES OF THE DISCLOSED SOLUTIONS

Figure 1:
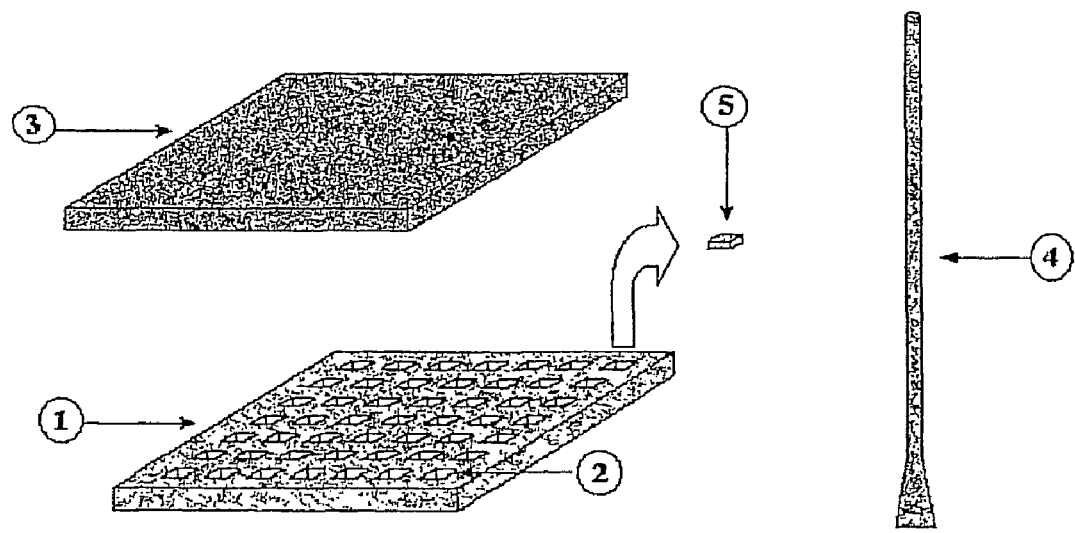
FIG. 1. Scheme of the mold to cast the miniplugs. The sheet, with the stamped depressions, to pour the agarose-cell suspension is shown in the bottom of the figure. In the top, are shown the mold lid and a miniplug. The spatula to distribute the agarose-cell suspension is also shown in the right.
Figure 2:
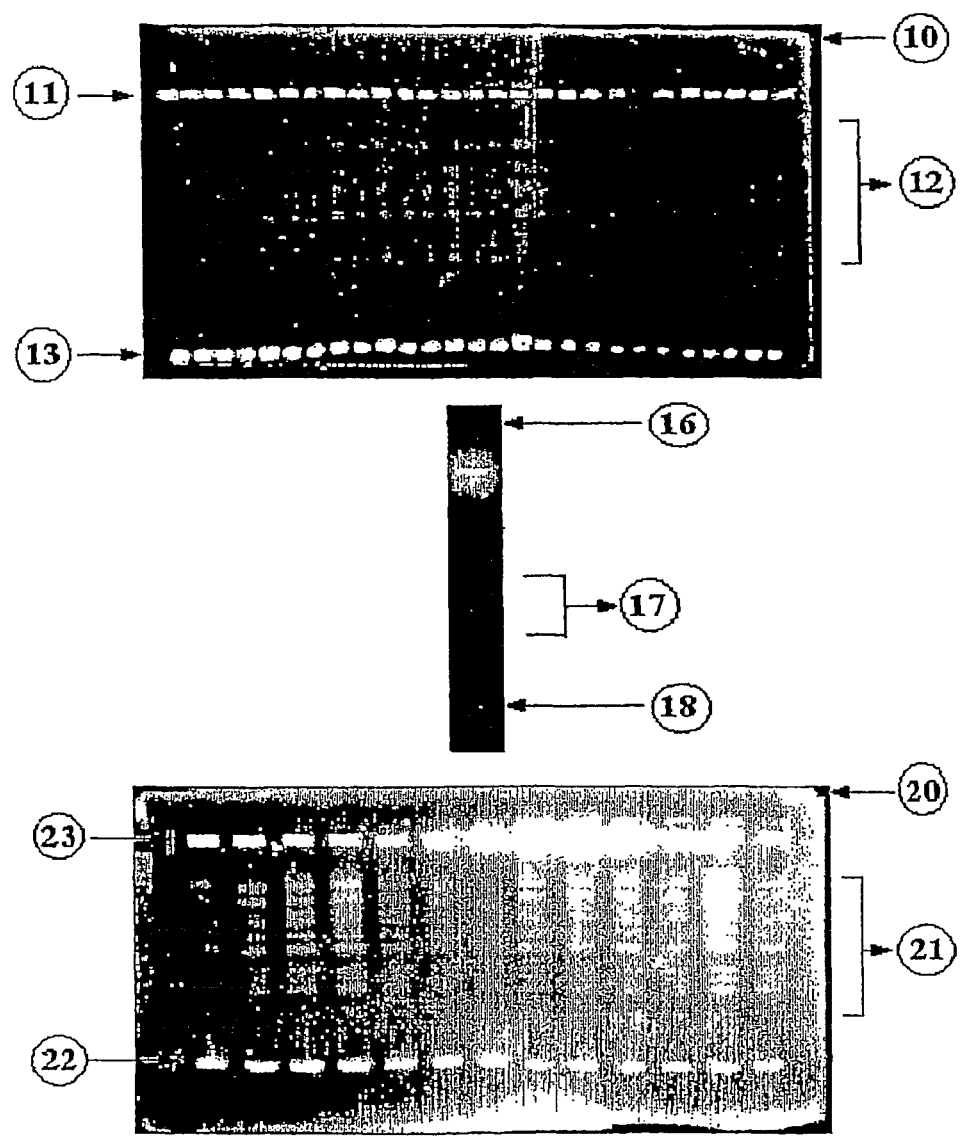
FIG. 2. Photograph of *S. cerevisiae* and *H. polymorpha* chromosomal band patterns separated in the miniCHEF and miniTAFE minigels. Top of the figure: miniCHEF minigel with 7 cm wide, its 27 slots and the band patterns of *S. cerevisiae* chromosomes. The minigel, 4 cm in width, and the band patterns of *H. polymorpha* chromosomes are shown in the center of the figure. The samples were prepared by the non-enzymatic method by incubating the miniplugs containing immobilized cells with NDSU. Running conditions: 10 V/cm, 20° C., 1.5% agarose, 0.5×TBE, 50 seconds of pulse time and 4 hours of electrophoresis. In the bottom of the figure, the miniTAFE minigel with the band patterns of *S. cerevisiae* chromosomes is shown. In the MiniTAFE, 10 V/cm, 1.5% agarose, 0.5×TBE, 60 seconds of pulse time and 6 hours of electrophoresis were used. The samples were prepared by incubating the cells with NDSU and later embedding them in agarose miniplugs.
Figure 3:
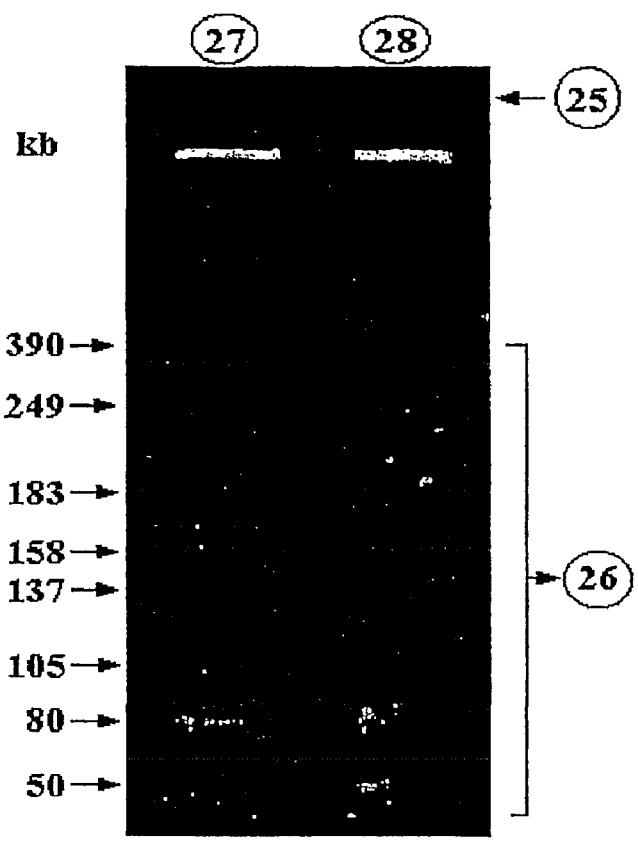
FIG. 3. Band patterns obtained in the miniCHEF for the Xba I macrorestriction DNA fragments of *P. aeruginosa*. In the left, *P. aeruginosa* miniplugs were prepared from cells grown in liquid LB medium, whereas, in the right, the miniplugs were prepared from cells grown on LB plates. MiniCHEF was used at 10 V/cm, 20° C., 1.5% agarose and 0.5×TBE, and pulse ramps of 20, 15, 10, 5 and 3 seconds and 5, 15, 320, 1020 and 100 pulses were applied, respectively.
Figure 4:
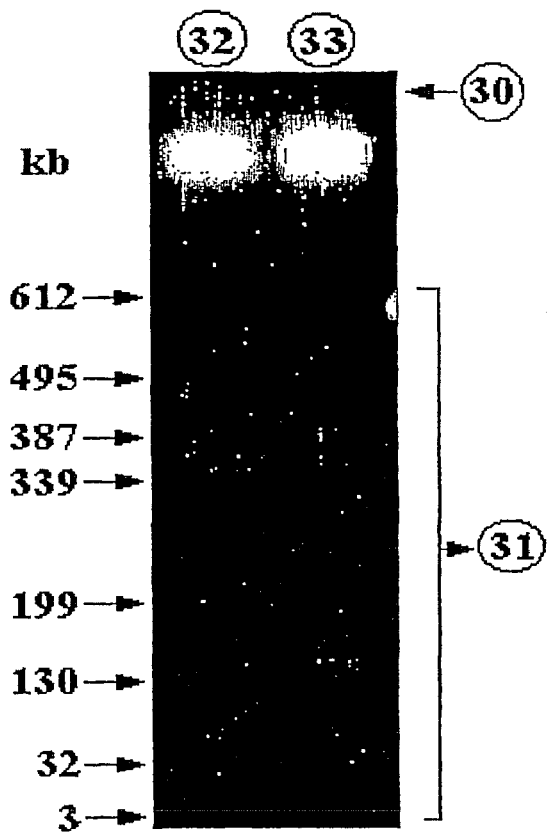
FIG. 4. Band patterns given by MiniCHEF for Sma I macrorestriction DNA fragments of *S. aureus*. Band patterns of samples prepared by the non-enzymatic method by incubating the miniplugs containing cells with NDSUPlus are shown in the left. Band patterns of samples prepared by incubating the cells with NDSUPlus and later embedding them in agarose miniplugs are shown in the right. In both sample preparations, the cells were cultured on plates. Running conditions were 10 V/cm, 20° C., 1.5% agarose, 0.5×TBE, pulse times of 1, 5, 9, 13, 17 and 21. In each ramp, were applied 130 pulses.
Figure 5:
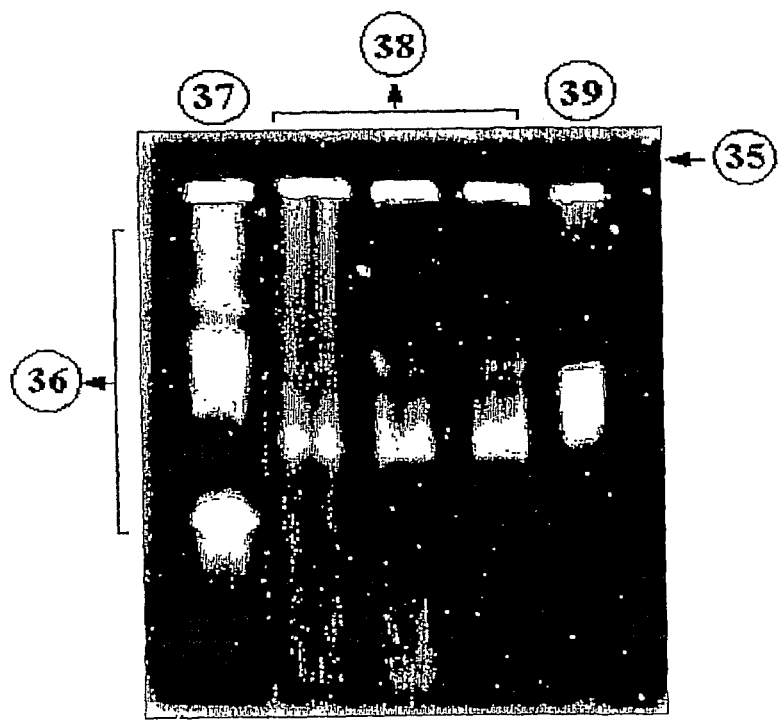
FIG. 5. Photograph of the DNA band patterns of *E. histolytica, S. cerevisiae* and O-phage concatamers. Electrophoresis was performed in the minigel of the miniTAFE at 9.03 V/cm electric field strength, 120 s pulse time, 20° C., 1% agarose (SeaKem), 0.5×TBE buffer and 6 hours of electrophoresis. Samples of 0.1 cm thickness were loaded. From left to right, lane 1: Miniplugs from *S. cerevisiae* 196-2; lanes 2, 3, 4 and 5: Miniplugs containing *E. histolytica* trophozoites incubated with NDSUPlus at 45° C. for 0.5, 1, 2 and 16 hours, respectively, lane 6: O DNA ladders.
Figure 6:
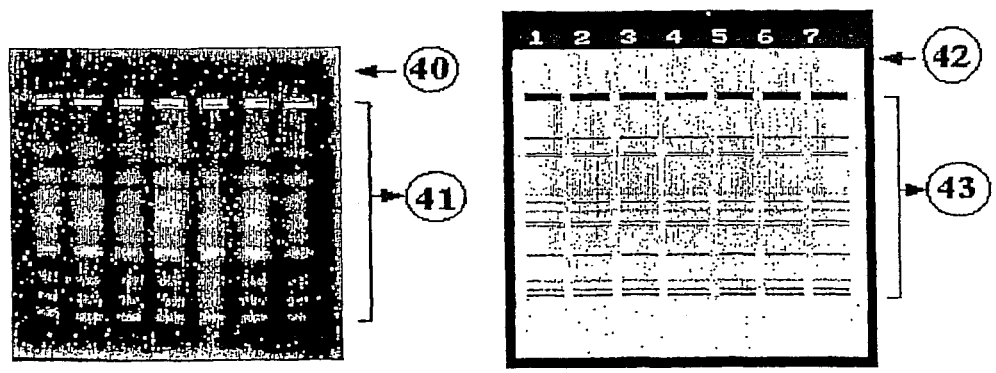
FIG. 6. Photograph of real miniCHEF minigel (40) used to obtain the band patterns of *S. cerevisiae* 196-2 chromosomes (left) and graphic of the hypothetical minigel (42) predicted by the simulator (right). Real electrophoresis was performed at the conditions predicted by simulator. Immobilized intact DNA molecules of *S. cerevisiae* 196-2, analyzed in this electrophoresis run, were prepared by the non-enzymatic procedure disclosed in this invention. For 10 V/cm electric field strength and 20° C. buffer temperature, the running conditions predicted by simulator were four pulse ramps of 5, 40, 75 and 110 seconds and 42 pulses in every ramp. The migration data and the color code used to identify the sizes of the molecules are shown in Table II.
Figure 7:
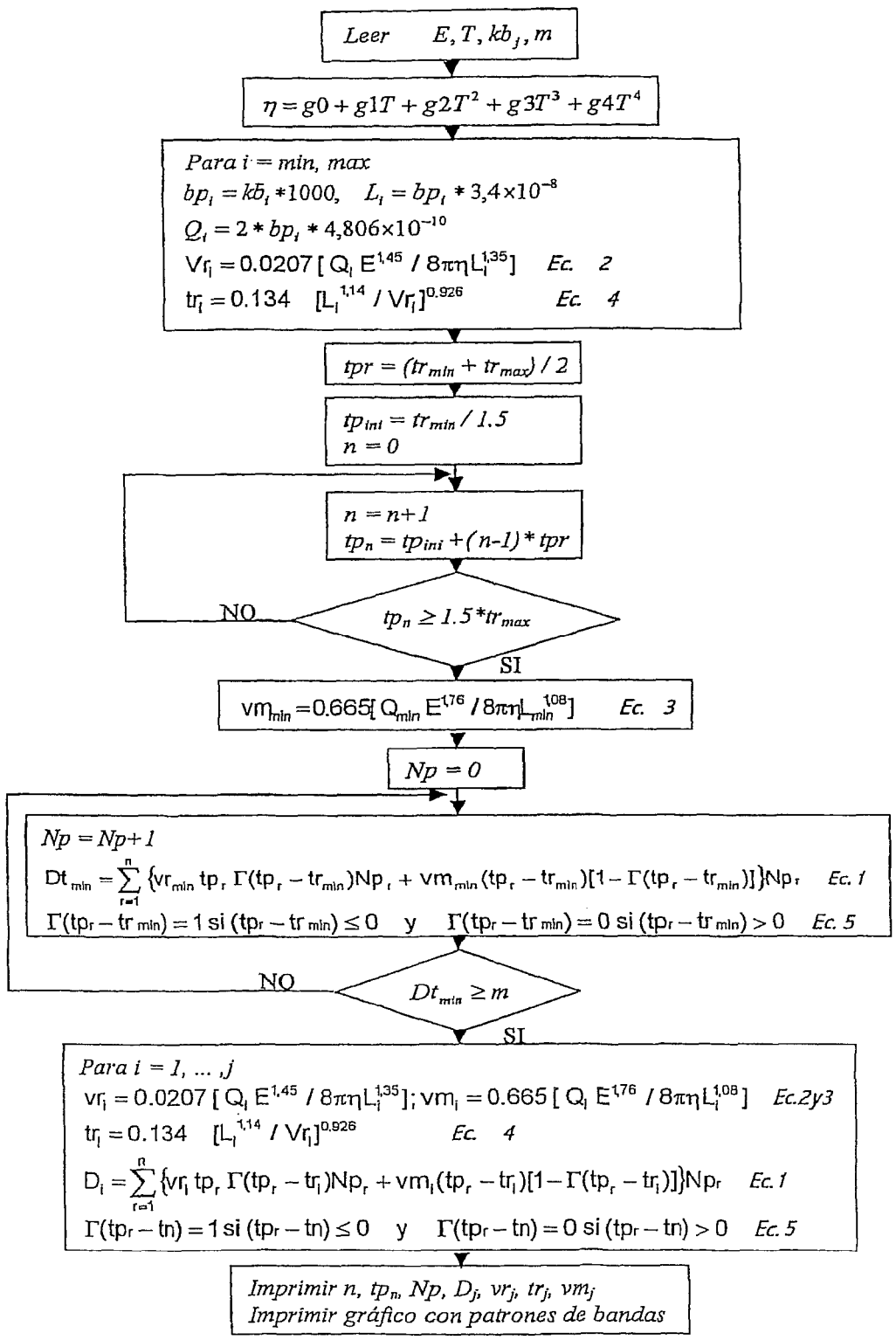
FIG. 7. Flow chart of the method to simulate the DNA band patterns in the minigels of the miniCHEF. The following parameters and variables are used in the diagram: DNA size (kb), DNA reorientation times (tr), DNA migration velocity during reorientation (vr), and after reorientation (vm) in the miniCHEF. Additionally, $tp_r$: pulse time in each ramp, $Np_r$: number of pulses in each ramp, g0, g1, g2, g3, g4 coefficients obtained to describe viscosity (K) as function of the experimental temperature (T), Dt: theoretical distance predicted by the method, n: number of ramps, E: electric field, L: DNA contour length, bp: base pairs, Q: DNA net charge.
Figure 8:
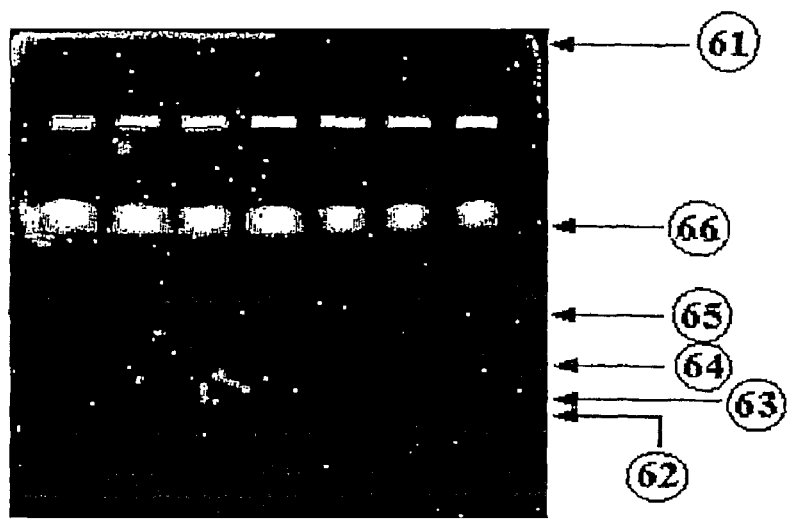
FIG. 8. Electrophoresis karyotype (61) obtained in the miniCHEF for *S. cerevisiae* chromosomes. Electrophoresis conditions: 10 V/cm, 1.5% agarose gel, 0.5×TBE, 20° C., 2.95 seconds and 453 pulses and 21.56 seconds and 453 pulses.
Figure 9:
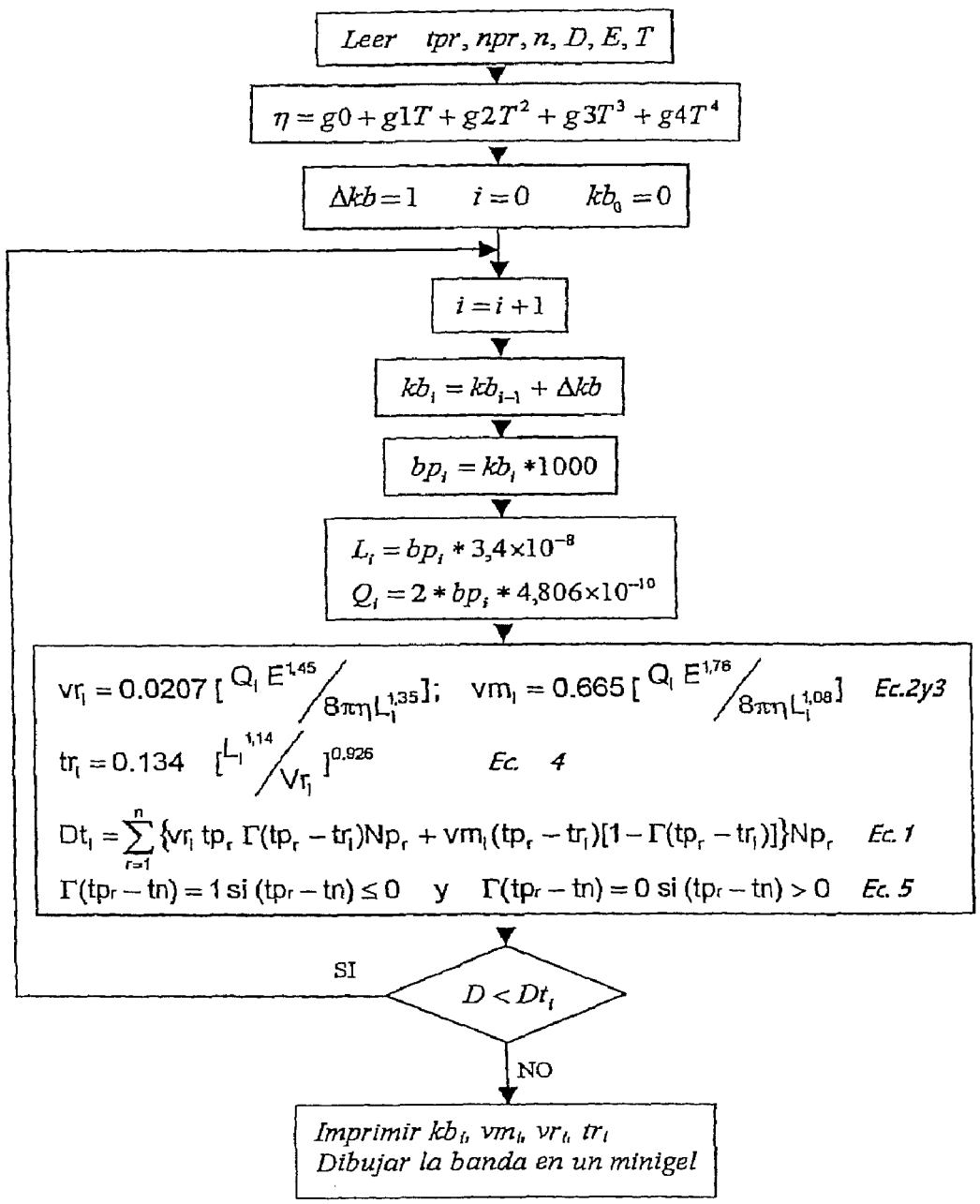
FIG. 9. Flow chart of the method that needs to be fed with migrated distances to estimate the size (kb), reorientation times (tr), migration velocity during reorientation (vr) and after reorientation (vm) of the molecules separated in the miniCHEF. $tp_r$: pulse time in each ramp, $Np_r$: number of pulses in each ramp, g0, g1, g2, g3, g4 coefficients obtained to describe viscosity (K) as function of the experimental temperature (T), D: distance migrated in the gel by DNA molecules, Dt: theoretical migrated distance predicted by the simulator, n: number of ramps, E: electric field, L: DNA contour length, bp: base pairs, Q: DNA net charge.
Figure 10:
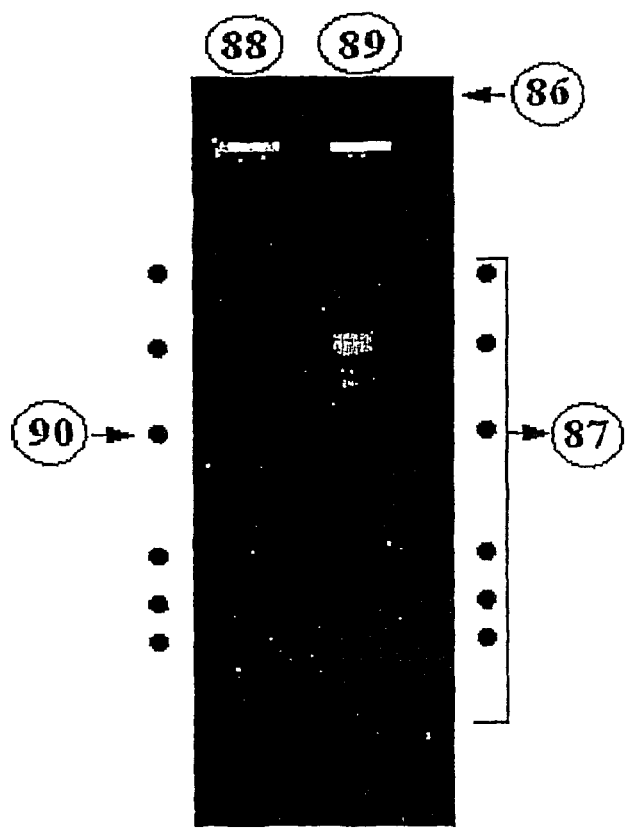
FIG. 10. MiniCHEF typing of the INN3 and INN7 *E. coli* isolates after Xba I restriction digestion of their DNA molecules. The non-enzymatic method to prepare the samples was used. Running conditions were: 10 V/cm, 20° C., 1.5% agarose gel and 0.5×TBE, applying pulse ramps of 25, 20, 15, 10 and 5 seconds and 35, 40, 50, 140 and 800 pulses, respectively. Points (90) tag the restriction fragments that both isolates have in common

1—Preparation of intact DNA molecules of microorganisms, embedded in thin miniplugs of any gel, is performed between 5 minutes and 1 hour. The preparation does not require the uses of enzymes, then it is performed rapid and at low cost.

2—Non-enzymatic preparation of DNA samples for PFGE is efficient using cells grow in liquid or solid media. Some type of cells can be incubated in the non-enzymatic solutions prior to their embedding. This modification reduces the time necessary to prepare the samples.

3—Gel-embedded DNA molecules, prepared by the disclosed procedure, are free of restriction endonuclease inhibitors. These molecules are digested by restriction enzymes in 2 hours, giving their typical band patterns in pulsed field gel electrophoresis experiments performed in miniequipments.

4—Homogenously sized miniplug, containing immobilized DNA from microorganisms, are obtained, thus they do not need to be cut prior to the electrophoresis. Identical miniplugs guarantee the reproducibility of the results.

5—Molecular karyotypes or pulsetypes of many samples (up to 27) are obtained in run time ranging from 2.5 to 7 hours. The consume of buffer and matrix of separation is low. The time required for separation depends on the microorganism studied and the miniequipment used, as well as on the electric field, running temperature and pulse time ramps used.

6—The equipments that are used to analyze the genome of microorganisms through pulsed field minigel electrophoresis in miniequipments require small laboratory bench space.

7—The band patterns can be simulated in the computer as many times as required, previously to perform the experiments. The simulation permits to select the electric field, temperature and pulse time ramps that result in the best separation among the molecules without expenses of reagents and biological samples.

8—The selection of the pulse ramps is performed with the aid of a method based on equations that describe migration of DNA molecules in the miniCHEF minigels. Then, the method to select the ramps gives the picture of the optimal pattern of separation among the molecules.

9—Size markers are dispensable to estimate the sizes, reorientation times and migration velocities of DNA molecules. The method disclosed here to estimate these parameters, based on the distances migrated by the molecules in the gel, provide these information. The method can be applied when any condition of pulse ramps and electric field strength between 1-20 V/cm, temperature between 4-30° C. were used in the electrophoresis, but it demands that the experiment were done in 1.5% agarose gel and 0.5×TBE.

10—The bands resolved in the electrophoresis patterns can be characterized by the size of the molecules migrating in each band, the reorientation times of said molecules and their migration velocities.

11—The process disclosed herein saves time, chemical reagents and biological samples.

12—The process, that includes DNA sample preparation and the analysis of the genome of 27 microorganisms, takes a single working day.

13—A kit of reagents, to simplify intact DNA preparation of microorganisms, is provided.

The invention claimed is:

1. A process for rapid bacterial typing by Pulsed Field Gel Electrophoresis (PFGE) performed in 7 to 13 hours and including the separation of bacterial DNA restriction fragments by electrophoresis in minichambers of CHEF (Contour Clamped Homogeneous Electric Field) system, electrophoresis performed in 1.5% agarose gels and 0.5×TBE buffer (44.5 mM Tris, 44.5 mM Boric Acid, 1 mM EDTA, pH 8.3); process wherein the improvement comprises a step for preparing, in agarose miniplugs, intact and immobilized DNA molecules from bacterial cells of the species *Pseudomonas aeruginosa*, *Escherichia coli* and *Staphylococcus aureus*, wherein said step of preparation further comprises steps of:

i) washing, embedding and incubating the bacterial cells and the DNA molecules in a plurality of lytic and protease enzymes-free solutions, composed by chemical reagents; wherein said solutions are:

(1) NaCl salt, at a concentration of 0.15M, and the metal chelating agent EDTA, at a concentration of 0.01M and pH 8.0;

(2) NaCl salt at a concentration of 0.15M;

(3) low melting agarose at a concentration of 1.5% suspended in NaCl solution at a concentration of 0.15M;

(4) low melting agarose at a concentration of 1.5% suspended in the solution that contains NaCl salt at a concentration of 0.15M and the metal chelating agent EDTA at a concentration of 0.01M and pH 8.0;

(5) the metal chelating agent EDTA at a concentration of 0.1M, two anionic detergents Sarkosyl and Nonidet P-40 both at a concentration of 1%, and 0.01M Tris base, pH 8.0;

(6) the metal chelating agent EDTA at a concentration of 0.1M, the two anionic detergents Sarkosyl and Nonidet P-40 both at a concentration of 1%, 0.01M Tris base, and 4M Urea, pH 9.5;

(7) the metal chelating agent EDTA at a concentration of 0.1M and 0.01M Tris base, pH 8.0;

ii) embedding said bacterial cells in agarose miniplugs by means of a flexible and sterilizable mold which has a lid and various square depressions stamped in one of its surfaces; mold that is flexible enough to be bent for detaching said miniplugs from it and is reusable after its sterilizing; and iii) casting in the mold said agarose miniplugs containing cells of one of said bacterial species, detaching said miniplugs from the mold, and incubating and washing the miniplugs with the solutions composed by chemical reagents.

2. The process of claim 1, wherein said *Pseudomonas aeruginosa* cells are grown in broth and collected by centrifugation for said preparation of the agarose-embedded intact DNA molecules.

3. The process of claim 1, wherein said *Pseudomonas aeruginosa* cells are grown in plates and collected by washing said plates for the preparation of the agarose-embedded intact DNA molecules.

4. The process of claim 1, wherein said *Staphylococcus aureus* cells are grown in plates and collected by washing said plates for the preparation of the agarose-embedded intact DNA molecules.

5. The process of claim 1, wherein said *Escherichia coli* cells are grown in broth and collected by centrifugation for said preparation of the agarose-embedded intact DNA molecules.

6. The mold of claim 1, wherein said mold sheet comprises silicone, rubber or any other flexible material.

7. The process of claim 1, wherein said lid for covering the mold is made of glass.

8. The process of claim 1, wherein the embedding of said bacterial cells in the agarose miniplugs, by means of using the flexible and sterilizable mold and its lid, comprises the following steps:
  i) pouring the suspension of the bacterial cells and agarose onto the stamped surface of the mold;
  ii) distributing said suspension evenly with a spatula to fill said depressions;
  iii) covering the mold with its lid and led to set until the miniplugs are formed; and
  iv) bending the mold onto a flask to detach the miniplugs.

9. The process of claim 1, wherein the washing of *Escherichia coli* cells is done with said solution (1) containing 0.15M NaCl and 0.01M EDTA, pH 8.0.

10. The process of claim 1, wherein the washing of *Staphylococcus aureus* cells is done with said solution (1) containing 0.15M NaCl and 0.01M EDTA, pH 8.0.

11. The process of claim 1, wherein the washing of *Pseudomonas aeruginosa* cells is done with said solution (2) containing 0.15M NaCl.

12. The process of claim 1, wherein the embedding of *Pseudomonas aeruginosa* cells is done with said solution (3) containing 1.5% low melting temperature agarose suspended in 0.15M NaCl.

13. The process of claim 1, wherein the embedding of *Escherichia coli* cells is done with said solution (3) containing 1.5% low melting temperature agarose suspended in 0.15M NaCl.

14. The process of claim 1, wherein the embedding of *Staphylococcus aureus* cells is done with said solution (4) containing 1.5% low melting temperature agarose suspended in 0.15M NaCl and 0.01M EDTA, pH 8.0.

15. The process of claim 1, wherein the incubating of the miniplugs containing *Escherichia coli* cells is done with said solution (5) containing 0.1M EDTA, 1% Sarcosyl, 1% Nonidet P-40 and 0.01M Tris base, pH 8.0.

16. The process of claim 1, wherein the incubating of the miniplugs containing *Escherichia coli* cells is done with said solution (6) containing 0.1M EDTA, 1% Sarcosyl, 1% Nonidet P-40, 0.01M Tris base and 4M Urea, pH 9.5.

17. The process of claim 1, wherein the incubating of the miniplugs containing *Pseudomonas aeruginosa* cells is done with said solution (6) containing 0.1M EDTA, 1% Sarcosyl, 1% Nonidet P-40, 0.01M Tris base and 4M Urea, pH 9.5.

18. The process of claim 1, wherein the incubating of the miniplugs containing *Staphylococcus aureus* cells is done with said solution (6) containing 0.1M EDTA, 1% Sarcosyl, 1% Nonidet P-40, 0.01M Tris base and 4M Urea, pH 9.5.

19. The process of claim 1, wherein the washing of the miniplugs containing the intact and immobilized DNA molecules of *Pseudomonas aeruginosa* is done with said solution (6).

20. The process of claim 1, wherein the washing of the miniplugs containing the intact and immobilized DNA molecules of *Staphylococcus aureus* is done with said solution (7) containing 0.1M EDTA and 0.01M Tris base, pH 8.0.

21. The process of claim 1, wherein the storing of the miniplugs containing the intact and immobilized DNA molecules of *Pseudomonas aeruginosa* is done with said solution (7) containing 0.1M EDTA and 0.01M Tris base, pH 8.0.

22. The process of claim 1, wherein said sterilizable mold comprises a sheet having the square depressions stamped in one of its surfaces, wherein said depressions are of 0.3 cm in size and from 0.03 to about 0.1 cm in depth, depressions into which the suspension of agarose-bacterial cell mix solidifies and provides miniplugs of said sizes.

23. The mold of claim 22, wherein said sheet comprises silicone, rubber or like flexible material, and comprises up to 49 identical square depressions stamped in one of its surfaces.

24. The process of claim 1, wherein said step of preparation, in the agarose miniplugs, of said intact and immobilized DNA molecules from *Pseudomonas aeruginosa* cells comprises the steps of:
  i) collecting said cells from broth or plates followed by washing the cells in the solution (2) containing 0.15M NaCl;
  ii) embedding of said cells in the solution (3) containing 1.5% low melting temperature agarose suspended in 0.15M NaCl and pouring the suspension onto said flexible mold;
  iii) incubating the miniplugs, after they are formed, for 30 minutes at 50° C. in the solution (6) containing 0.1M EDTA, 1% Sarcosyl, 1% Nonidet P-40, 0.01M Tris base and 4M Urea, pH 9.5; and
  iv) washing said miniplugs twice at 50° C. for 10 minutes in the solution (7) containing 0.1M EDTA and 0.01M Tris base, pH 8.0, and further storing them in said solution.

25. The process of claim 24, wherein said collecting of the cells in the step of preparation, in the agarose miniplugs, of the intact and immobilized DNA molecules from the *Pseudomonas aeruginosa* cells is done by centrifugation of the suspension of said cells grown in broth.

26. The process of claim 24, wherein said collecting of the cells in the step of preparation, in the agarose miniplugs, of the intact and immobilized DNA molecules from the *Pseudomonas aeruginosa* cells grown in plates is done by washing the plates with the solution (2) containing 0.15M NaCl and further centrifuging the cell suspension.

27. The process of claim 1, wherein the preparation of the intact and immobilized DNA molecules from the *Staphilococcus aureus* cells has the steps of:
  i) collecting said cells from plates by washing the plates with the solution (1) containing 0.15M NaCl and 0.01M EDTA, pH 8.0, and washing said cells in said solution;
  ii) embedding said cells in the solution (4) containing 1.5% low melting temperature agarose suspended in 0.15M NaCl and 0.01M EDTA, pH 8.0 and pouring the cell suspension onto the flexible mold;
  iii) incubating the miniplugs, after they are formed, for 60 minutes at 50° C. in the solution (6) containing 0.1M EDTA, 1% Sarcosyl, 1% Nonidet P-40, 0.01M Tris base and 4M Urea, pH 9.5; and
  iv) washing said miniplugs twice at 50° C. for 10 minutes in the solution (7) containing 0.1M EDTA and 0.01M Tris base, pH 8.0.

28. The process of claim 1, wherein the preparation of the intact and immobilized DNA molecules from the *Staphilococcus aureus* cells has the steps of:
  i) collecting said cells from plates by washing the plates with the solution (1) containing 0.15M NaCl and 0.01M EDTA, pH 8.0, and washing said cells in said solution;
  ii) preincubating said cells for 30 minutes at 50° C. in the solution (6) containing 0.1M EDTA, 1% Sarcosyl, 1%

Nonidet P-40, 0.01M Tris base and 4M Urea, pH 9.5, diluting fivefold the cell suspension with the solution (7) containing 0.1M EDTA and 0.01M Tris base, pH 8.0 and further collecting the preincubated cells by centrifugation;

iii) embedding said preincubated cells in the solution (4) containing 1.5% low melting temperature agarose suspended in 0.15M NaCl and 0.01M EDTA, pH 8.0 and pouring the cell suspension onto the flexible mold; and iv) washing the miniplugs, after they are formed, twice at 50° C. for 10 minutes in the solution (7) containing 0.1M EDTA and 0.01M Tris base, pH 8.0.

29. The process of claim 1 wherein said step of preparation, in the agarose miniplugs, of the intact and immobilized DNA molecules from *Escherichia coli* cells is done according to the steps of:

i) collecting said cells from broth followed by washing the cells in the solution (1) containing 0.15M NaCl and 0.01M EDTA, pH 8.0;

ii) embedding said cells in the solution (3) containing 1.5% low melting temperature agarose suspended in 0.15M NaCl and pouring the suspension onto the flexible mold;

iii) incubating the miniplugs, after they are formed, for 10 minutes at 37° C. in the solution (5) containing 0.1M EDTA, 1% Sarcosyl, 1% Nonidet P-40 and 0.01M Tris base, pH 8.0; and iv) incubating said miniplugs for 30 minutes at 50° C. in the solution (6) containing 0.1M EDTA, 1% Sarcosyl, 1% Nonidet P-40, 0.01M Tris base and 4M Urea, pH 9.5.

30. A process for rapid bacterial typing by Pulsed Field Gel Electrophoresis (PFGE) performed in 7 to 13 hours and including the separation of bacterial DNA restriction fragments by electrophoresis in minichambers of CHEF (Contour Clamped Homogeneous Electric Field) system, wherein the improvement comprises a step for preparing, in agarose miniplugs, intact and immobilized DNA molecules from bacterial cells of the species *Pseudomonas aeruginosa, Escherichia coli* and *Staphylococcus aureus*, wherein said step of preparing further comprises the steps of:

i) washing, embedding and incubating the bacterial cells and the DNA molecules in a plurality of lytic and protease enzymes-free solutions, wherein said solutions are:

(1) NaCl and the metal chelating agent EDTA at pH 8.0;
(2) NaCl at a concentration of 0.15M, without the metal chelating agent EDTA;
(3) low melting agarose suspended in a NaCl solution;
(4) low melting agarose suspended in a NaCl solution and further comprising the metal chelating agent EDTA at pH 8.0;
(5) the metal chelating agent EDTA and two anionic detergents at pH 8.0;
(6) the metal chelating agent EDTA, the two anionic detergents and Urea at pH 9.5; and
(7) the metal chelating agent EDTA, at pH 8.0.

ii) embedding said bacterial cells in agarose miniplugs by means of a flexible and sterilizable mold which has a lid and various square depressions stamped in one of its surfaces; mold that is flexible enough to be bent for detaching said miniplugs from it and is reusable after its sterilizing; and iii) casting in the mold said agarose miniplugs containing cells of one of said bacterial species, detaching said miniplugs from the mold, and incubating and washing the miniplugs with the solutions composed by chemical reagents.

31. The process of claim 30, wherein one of the two variants for preparing, in the agarose miniplugs, the intact and immobilized DNA molecules from the *Staphylococcus aureus* cells has the steps of:

i) collecting said cells from plates by washing the plates with the solution (1), and washing said cells in said solution;

ii) embedding said cells in the solution (4) and pouring the cell suspension onto the flexible mold;

iii) incubating said miniplugs for 60 minutes at 50° C. in the solution (6); and iv) washing said miniplugs twice at 50° C. for 10 minutes in the solution (7).

32. The process of claim 30, wherein one of the two variants for preparing the agarose miniplugs, the intact and immobilized DNA molecules from the *Staphylococcus aureus* cells has the steps of:

i) collecting said cells from plates by washing the plates with the solution (1) containing 0.15M NaCl and 0.01M EDTA, pH 8.0, and washing said cells in said solution;

ii) embedding said cells in the solution (4), and pouring the cell suspension onto the flexible mold;

iii) incubating said miniplugs for 60 minutes at 50° C. in the solution (6); and washing said miniplugs in the solution (7).

* * * * *